(12) United States Patent
Grimes

(10) Patent No.: US 6,273,915 B1
(45) Date of Patent: Aug. 14, 2001

(54) FEMORAL HEAD-NECK PROSTHESIS AND METHOD OF IMPLANTATION

(76) Inventor: James B. Grimes, 15301 Vista Grande Dr., Bakersfield, CA (US) 93306

( * ) Notice: Subject to any disclaimer, the term of this patent is extended or adjusted under 35 U.S.C. 154(b) by 0 days.

(21) Appl. No.: 09/242,221

(22) PCT Filed: Aug. 13, 1997

(86) PCT No.: PCT/US97/14233

§ 371 Date: Jun. 21, 1999

§ 102(e) Date: Jun. 21, 1999

(87) PCT Pub. No.: WO98/06359

PCT Pub. Date: Feb. 19, 1998

Related U.S. Application Data

(60) Provisional application No. 60/023,398, filed on Aug. 13, 1996.

(51) Int. Cl.[7] ................................. A61F 2/32; A61F 2/36
(52) U.S. Cl. .................................. 623/23.21; 623/23.11; 623/23.15
(58) Field of Search ........................ 623/22.11, 23.11, 623/23.12, 23.15, 23.18, 23.21, 23.22, 23.31, 23.29, 23.4, 23.44, 23.53

(56) References Cited

U.S. PATENT DOCUMENTS

| | | | |
|---|---|---|---|
| 2,622,592 | * | 12/1952 | Rosenstein ........................ 623/23.11 |
| 2,650,588 | * | 9/1953 | Drew ................................ 623/23.11 |
| 2,679,245 | * | 5/1954 | Timmermans ..................... 623/23.11 |
| 2,682,265 | * | 6/1954 | Collison ........................... 623/23.11 |
| 2,685,877 | * | 8/1954 | Dobelle ............................ 623/23.11 |
| 2,947,308 | * | 8/1960 | Gorman ........................... 623/23.11 |
| 3,965,490 | | 6/1976 | Murray et al. . |
| 4,530,114 | * | 7/1985 | Tepic ...................................... 623/23 |
| 4,546,501 | * | 10/1985 | Gustilo et al. ......................... 623/23 |
| 4,664,668 | * | 5/1987 | Beck et al. ............................. 623/23 |
| 4,795,473 | * | 1/1989 | Grimes .................................. 623/23 |
| 4,998,937 | * | 3/1991 | Grimes .................................. 606/89 |
| 5,035,717 | | 7/1991 | Brooks . |
| 5,169,401 | | 12/1992 | Lester et al. . |
| 5,314,479 | * | 5/1994 | Rockwood, Jr. et al. ............. 623/19 |
| 5,376,125 | * | 12/1994 | Winkler ................................. 623/23 |
| 5,458,651 | * | 10/1995 | Lawes ................................... 623/23 |
| 5,480,452 | | 1/1996 | Hofmann et al. . |
| 5,507,829 | | 4/1996 | Thongpreda et al. . |
| 5,658,349 | * | 8/1997 | Brooks et al. ......................... 623/23 |
| 5,725,595 | * | 3/1998 | Gustilo ................................. 623/23 |
| 5,980,575 | * | 11/1999 | Albrektsson et al. ................ 623/23 |

FOREIGN PATENT DOCUMENTS

| 1099519 | * | 11/1988 | (FR) | ....................... 623/23 |
|---|---|---|---|---|
| 2203943 | * | 11/1988 | (GB) | ....................... 623/23 |

OTHER PUBLICATIONS

International Search Report from PCT/US97/14233, Sep. 23, 1997, pp. 1.

* cited by examiner

Primary Examiner—Gene Mancene
Assistant Examiner—Michael B. Priddy
(74) Attorney, Agent, or Firm—Senniger, Powers, Leavitt & Roedel

(57) ABSTRACT

A femoral head-neck prosthesis (1) which allows natural straining of the upper femur to prevent bone loss. The natural angle of loading of the bone is determined prior to the operation, and the prosthesis is implanted with its longitudinal axis (AX-1) parallel to the natural angle (AX-5). The prosthesis is constructed to inhibit axial fixation and "splinting" of the prosthesis below the interface between the femur neck and the prosthesis on the upper femur. Splines (19) on a stem (13) of the prosthesis help to fix the prosthesis against rotation and toggling motion. The prosthesis is asymmetrical about its longitudinal axis to provide further stability when implanted. The prosthesis and its method of implantation preserve the trochanter and cap the femur to prevent microscopic debris from entering the interior bone.

29 Claims, 40 Drawing Sheets

FIG.4J
FIG.4I
FIG.4K
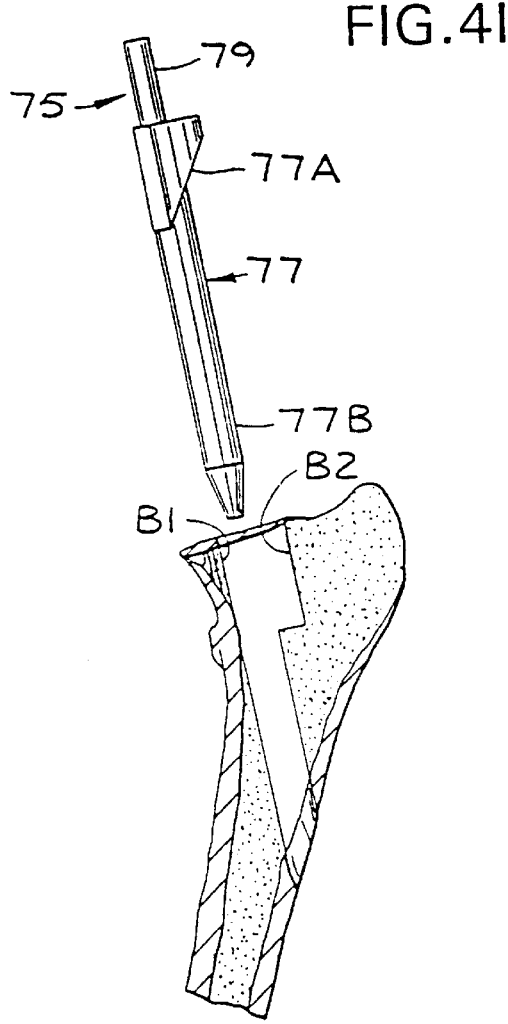
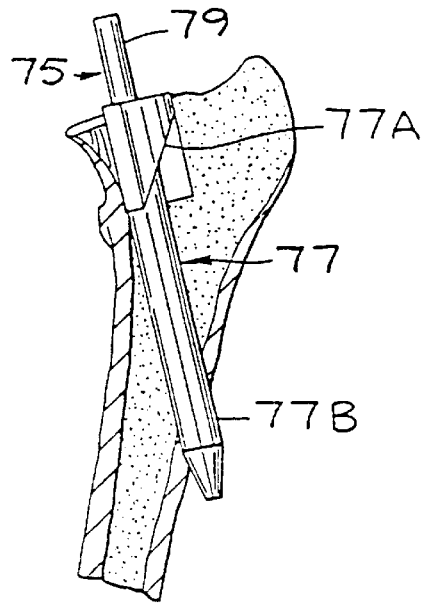
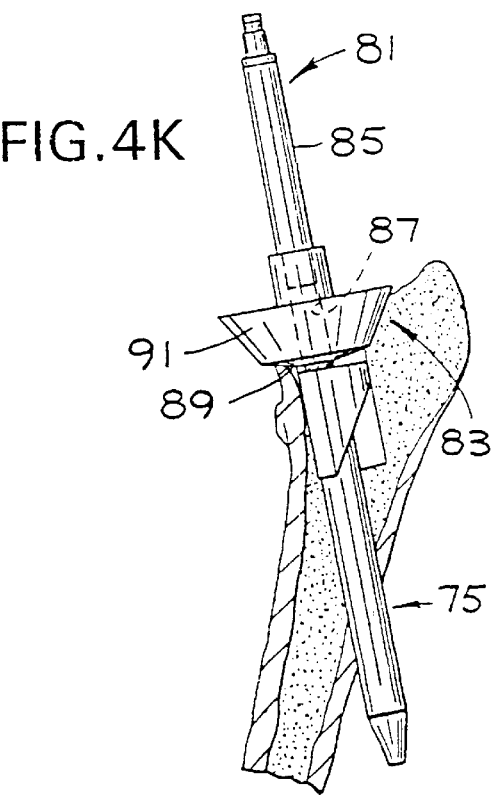

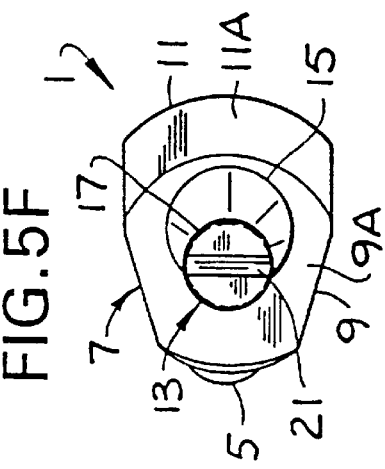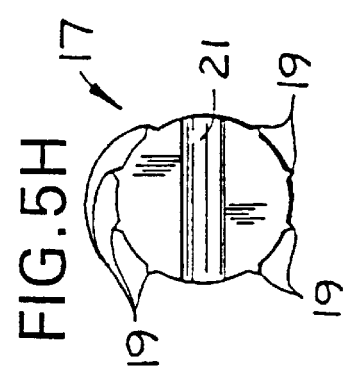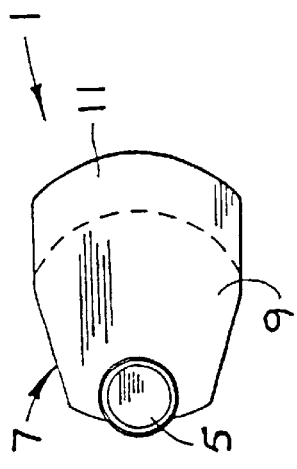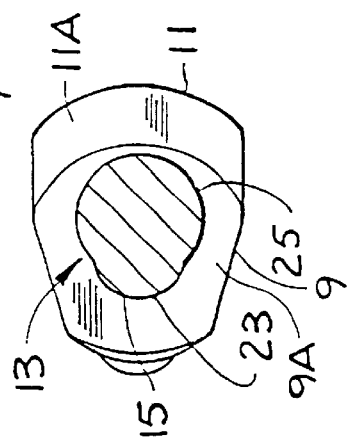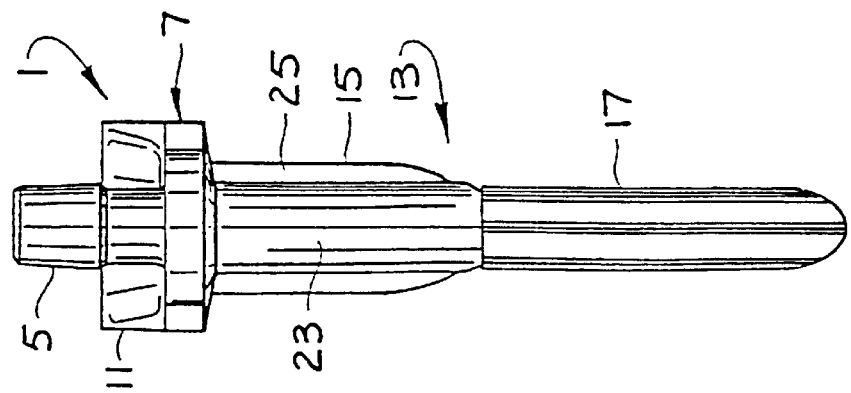

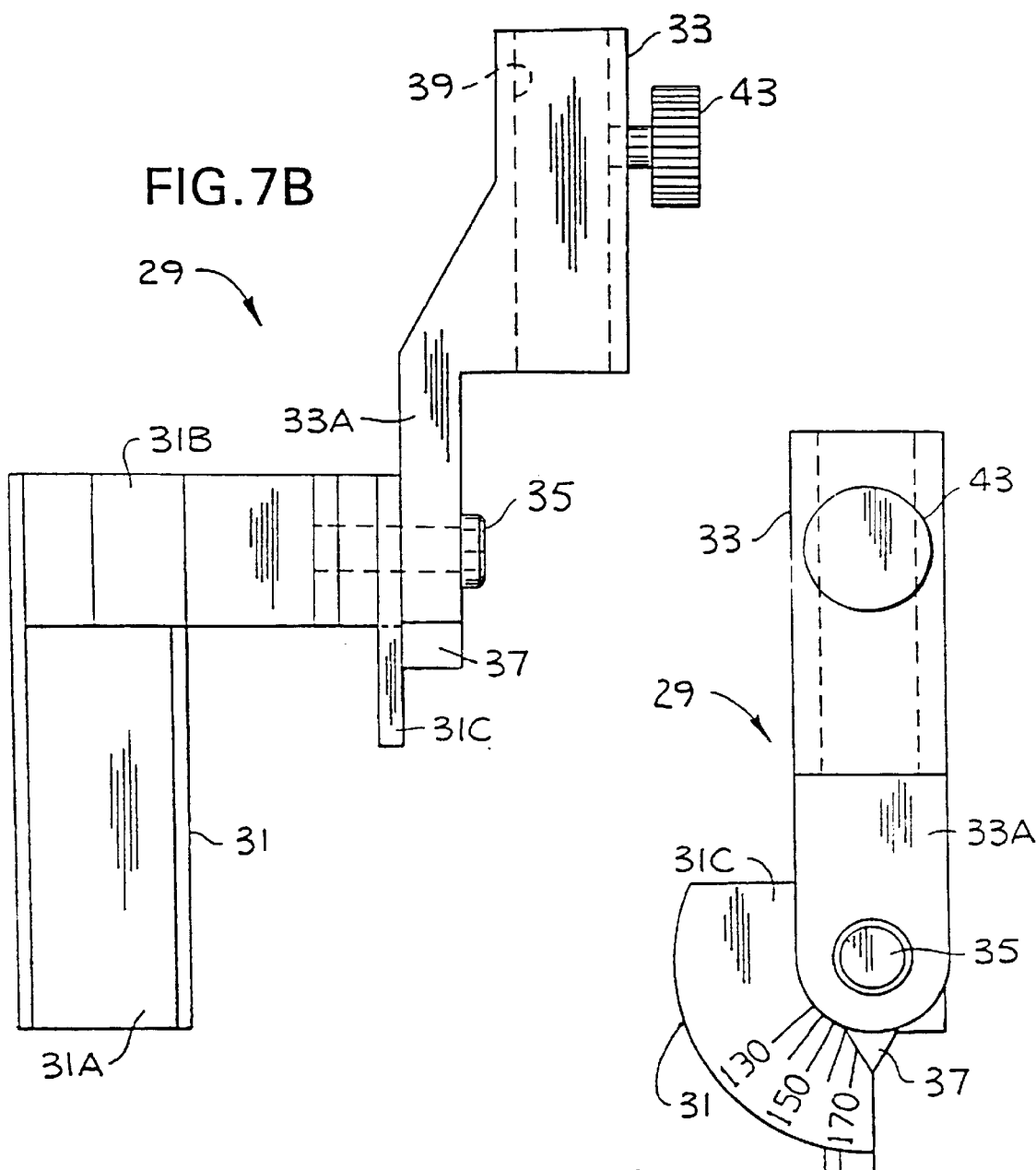

FIG.16A
FIG.16B
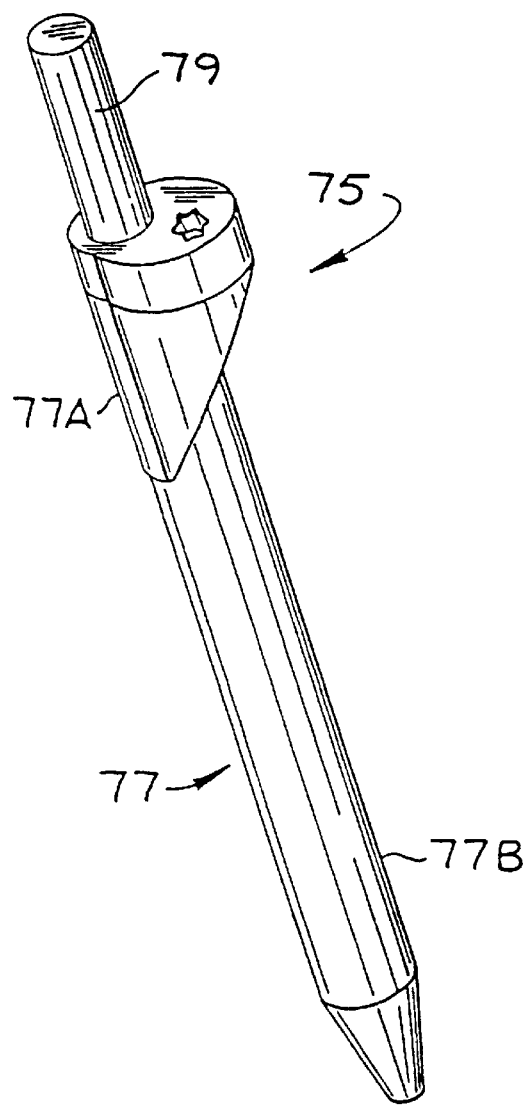
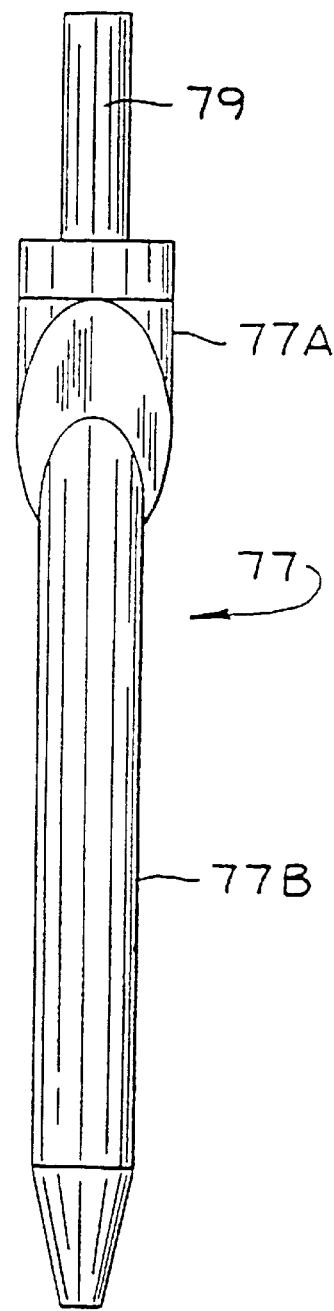

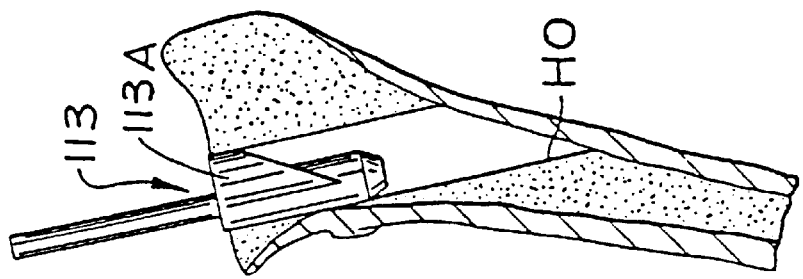
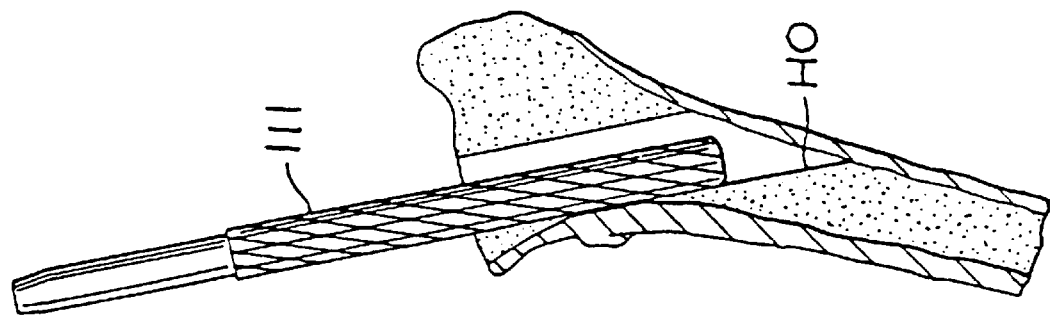
FIG.18F
FIG.18E

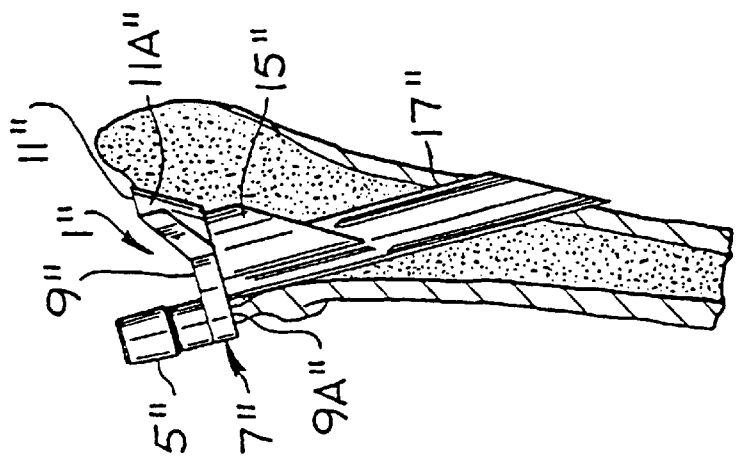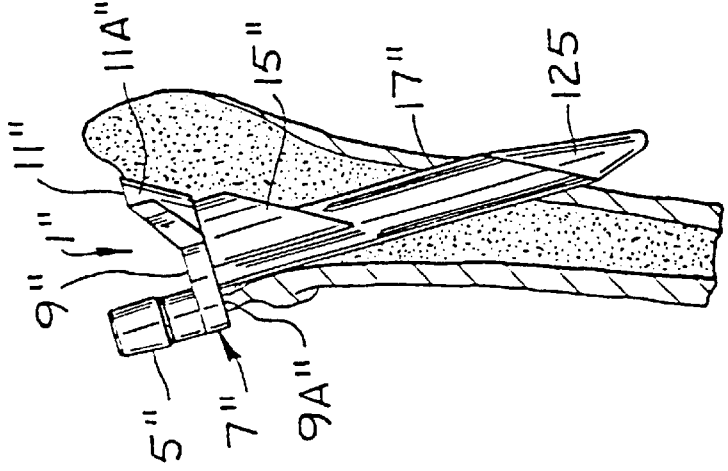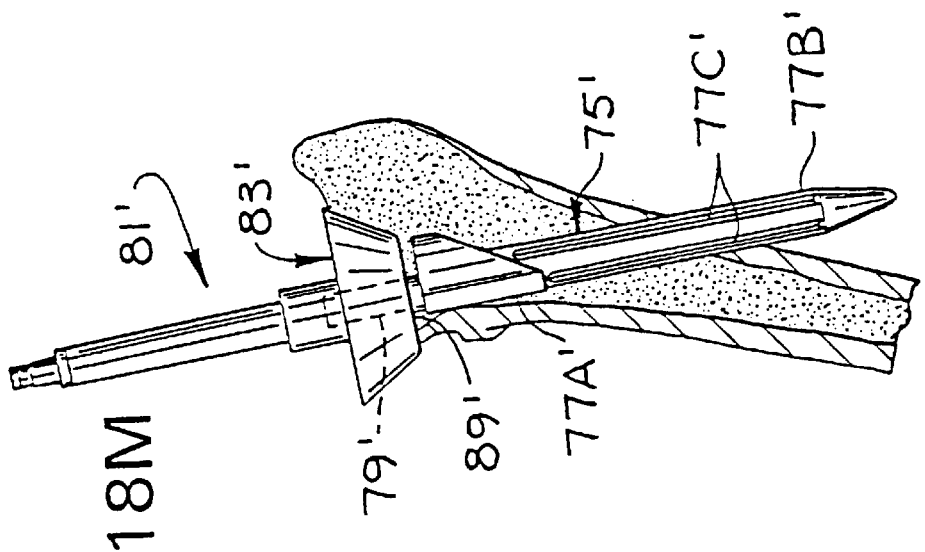

FEMORAL HEAD-NECK PROSTHESIS AND METHOD OF IMPLANTATION

This application is a continuation-in-part of U.S. application Ser. No. 60/023,398 filed Aug. 13, 1996 which is incorporated herein by reference.

BACKGROUND OF THE INVENTION

This invention relates generally to femoral head-neck prostheses and methods for their implantation.

Total hip replacement became a clinical reality for the first time in November, 1963, because of "cement fixation" of the components. The femoral head and neck were removed, the upper marrow canal of the femur was cleaned out (i.e., marrow contents removed), acrylic cement was poured into the marrow canal of the femur, and the metal femoral component was inserted into the liquid cement. In 10 to 15 minutes, the acrylic (methylmethacrylate) cement hardened and provided fixation for the femoral stem. The acrylic cement is similar to the acrylic dentists use to make dentures. Today, cement fixation of femoral components is still the most common means of fixation of the implant to the bone.

Cement fixation is the ultimate in form-filling contact with the bone. The liquid cement touches the entire inner surface of the upper femur. This type of fixation is generally successful for the short term (ten years), however in the long run, deterioration of the bone occurs and the cement and femoral component may loosen. Bone loss is caused by the cement and implant splinting the upper femur, preventing the upper femur from being subjected to natural bending. This is particularly a problem with younger patients (i.e., less than 50 years old).

Non-cemented or "press-fit" femoral components basically try to do the same thing as cemented implants; achieve solid fixation between the implant and the bone by maximally filling the medullary canal with the metal implant. In other words, the thinking is that the more closely and completely the metal implant fills the medullary canal, the better the fixation will be, and the more successful the result will be. However, experience shows this is not always the case.

The non-cemented femoral stems are larger and thicker than their cemented counterparts because the more flexible layer of acrylic cement is replaced with metal. Because a non-cemented stem is made of the same material and has a greater diameter than the cemented stem, it is stiffer. The greater the stiffness, the worse the splinting of the upper femur from the normal bending deflection that occurs in walking (strain). Although acceptable clinical results are achieved with non-cemented intramedullary femoral stems, non-cemented stems enerally have a more rapid rate of bone loss in the upper femur due to strain deprivation or what is commonly but incorrectly referred to as "stress shielding."

In summary, the fixation of all conventional intramedullary total hip femoral components depends on maximally filling the upper femur and the medullary canal with either cement and metal or metal alone. Not coincidentally, bone loss occurs with all of these implants.

SUMMARY OF THE INVENTION

Among the several objects and features of the present invention may be noted the provision of a femoral head-neck prosthesis which protects the femur from bone loss; the provision of such a prosthesis which provides stable seat between the prosthesis and the neck of the femur; the provision of such a prosthesis which accommodates compression at its interface with the upper femur; the provision of such a prosthesis which inhibits splinting of the upper femur; the provision of such a prosthesis which inhibits total axial fixation of the prosthesis below the seat; the provision of such a prosthesis which receives loads from the hip almost completely in compression; and the provision of such a prosthesis which has a longer useful life.

Further among the several objects and features of the present invention may be noted the provision of a method for implanting a femoral head-neck prosthesis which considers the historical loading of the femur; the provision of such a method which results in loads applied to the prosthesis being transmitted in a substantially natural way to the femur; the provision of such a method which permits a stable interface between a collar of the prosthesis and the femur neck for transmission of loads to the neck and upper femur; the provision of such a method which inhibits total axial fixation of the prosthesis; the provision of such a method which substantially reduces bending moments on the prosthesis as implanted; and the provision of such a method which causes the prosthesis to be loaded almost completely in compression.

Generally, a femoral prosthesis for implantation in a femur comprises a neck adapted to receive a prosthetic head thereon, a collar on which the neck is mounted and a stem extending from the collar on the opposite side of the collar from the neck. The prosthesis has a longitudinal axis corresponding to the longitudinal axis of the stem. The stem is constructed and arranged to fix the prosthesis from movement about its longitudinal axis and about axes perpendicular to the longitudinal axis, and to inhibit axial fixation of the prosthesis upon implantation in the femur, thereby to achieve substantially natural loading of the upper femur.

Another aspect of the present invention is a method for implanting a non-cemented femoral head-neck prosthesis in a femur, the femur having a shaft and a neck at the upper end of the shaft at the medial side of the femur. Generally, the method includes the steps of determining the axis of the medial trabecular stream of the femur, and cutting the neck of the femur to form a seat on the femur neck. A first bore is drilled through the shaft of the femur to extend from the neck of the femur down toward the lateral side of the femur along a line substantially parallel to the axis of the medial trabecular stream. A second bore is drilled through the shaft of the femur to extend from the neck of the femur down toward the lateral side of the femur along a line substantially parallel to the axis of the medial trabecular stream but spaced from the line of the first bore. A stem of the prosthesis is inserted in one of the first and second bores extending through the shaft to the lateral side of the femur, with a portion of the stem being received in the other of the first and second bores.

A fundamental aspect of this device is the stem being implanted in line with the normal loading trajectory of each individual hip in accordance with my prior U.S. Pat. No. 4,998,937. With the stem implanted in this orientation, the main forces on the implant will be end-on (i.e., in compression). In other words, with each step, the 500 pounds of force that a 150 pound man generates at the hip with normal walking is directed along the axis of the implant. The goal is to have the femoral neck receive 100% of the load (joint reaction force) through the collar. Force on the ball of the implant forces the collar against the resected femoral neck. The goal is to have the collar transmit all the load to the femoral neck so that the bone will receive 100% of the normal strain (bending).

Because so much load is transmitted through the collar, it is also important that the collar-bone interface be stable. In my previous patented (stem/barrel/plate) design, the barrel/ sideplate component stabilized the stem and collar. The barrel prevented the stem from toggling (forces which move the ball front to back or side to side) or rotating. The collar/stem component was free to be dynamically compressed against the femoral neck because the stem in the barrel offered little or no resistance to axial movement relative to the femur.

In my new invention, the upper femur takes the place of the barrel/sideplate in the prevention of toggling and rotation of the implant. The implant is constructed to mate with the machined upper femur so that toggle and rotation are controlled, but compression is permitted. The thick proximal stem makes contact with the inside of the femoral neck to prevent toggle and rotation. After cutting the femoral neck and removing all of the marrow contents, if you sight along the axis of loading, you will see a cavity in the femur which is generally oval in cross section. This oval cross-section can be substantially filled with two overlapping circles, one smaller than the other. The overlapping circles, extended along the axis of loading into three dimensions become two overlapping cylinders. The stem of my new femoral prosthesis has a double cylinder geometry. The upper femur cavity is machined to allow this double cylinder geometry to fit in the upper femur.

The geometry of the inside of the upper femur is variable from person to person. The goal is to have the surface of the double cylinder shaped upper stem of the prosthesis contact the bone of the femur in at least one point at all locations along the length of the upper stem. Because of the irregular shape of the bone, and because of the constraint of cylindrical reaming parallel to one axis (i.e., the load axis), implant-bone contact along the upper stem will be incomplete. The straight sides of the implant will contact the curving surfaces of the upper femur in only some discrete areas. This tangential contact is believed to be adequate to control toggle and rotational motion yet allow the bone to be compressed.

The machining of the upper femur basically comprises four basic drilling, reaming and circular planing operations.

Step 1. The medial femoral neck cavity is reamed on a first axis to fit the smaller of the two cylinders.

Step 2. A hole is drilled in femur on the same first axis.

Step 3. The lateral femoral neck cavity is reamed on a second axis parallel to the first to fit the larger of the two cross-sectional circles.

Step 4. The neck is "planed" to match the shape of the collar.

The implant is then inserted into the femur, with portions received in both of the cross-sectional circles.

Other objects and features of the present invention will be in part apparent and in part pointed out hereinafter.

BRIEF DESCRIPTION OF THE DRAWINGS

FIG. 4A is a view of the femur showing the axis of the medial trabecular stream;

FIG. 4I is a view showing the insertion of a calcar planing guide in the femoral neck;

FIG. 4J is the view of FIG. 4I, but with the calcar planing guide removed;

FIG. 4K is a view showing the calcar planing guide and the calcar planer for planing of the femoral neck;

FIG. 4R is a view showing the calcar planing guide and calcar planer for planing of the femoral neck;

FIG. 5D is a right side elevational view thereof;

FIG. 5E is a top plan view thereof;

FIG. 5F is a bottom plan view of the split stem prosthesis;

FIG. 5G is a sectional view of the split stem prosthesis taken in the plane of line 5G—5G in FIG. 5E;

FIG. 5H is an enlarged bottom end view of the stem of the split stem prosthesis showing splines on the stem;

FIG. 7B is a left side elevational view thereof;

FIG. 7C is a front elevational view thereof;

FIG. 16A is a perspective view of a calcar planing guide;

FIG. 16B is a left side elevational view thereof;

FIGS. 18A–18N and 18P illustrate a most preferred embodiment of a method for implanting the prosthesis;

FIG. 18A is a view of the femur showing the axis of the medial trabecular stream;

FIG. 18E is the view of FIG. 18D in vertical section with the angle guide removed;

FIG. 18F is a view showing sizing the femur for selection of the appropriate prosthesis;

FIG. 18M is a view showing the calcar planing guide and calcar planer for planing of the femoral neck;

FIG. 18N is a view illustrating installation of the prosthesis employing a removable bullet tip;

FIG. 18P is a view illustrating an installed prosthesis;

Corresponding reference characters indicate corresponding parts throughout the several views of the drawings.

Figure 1:
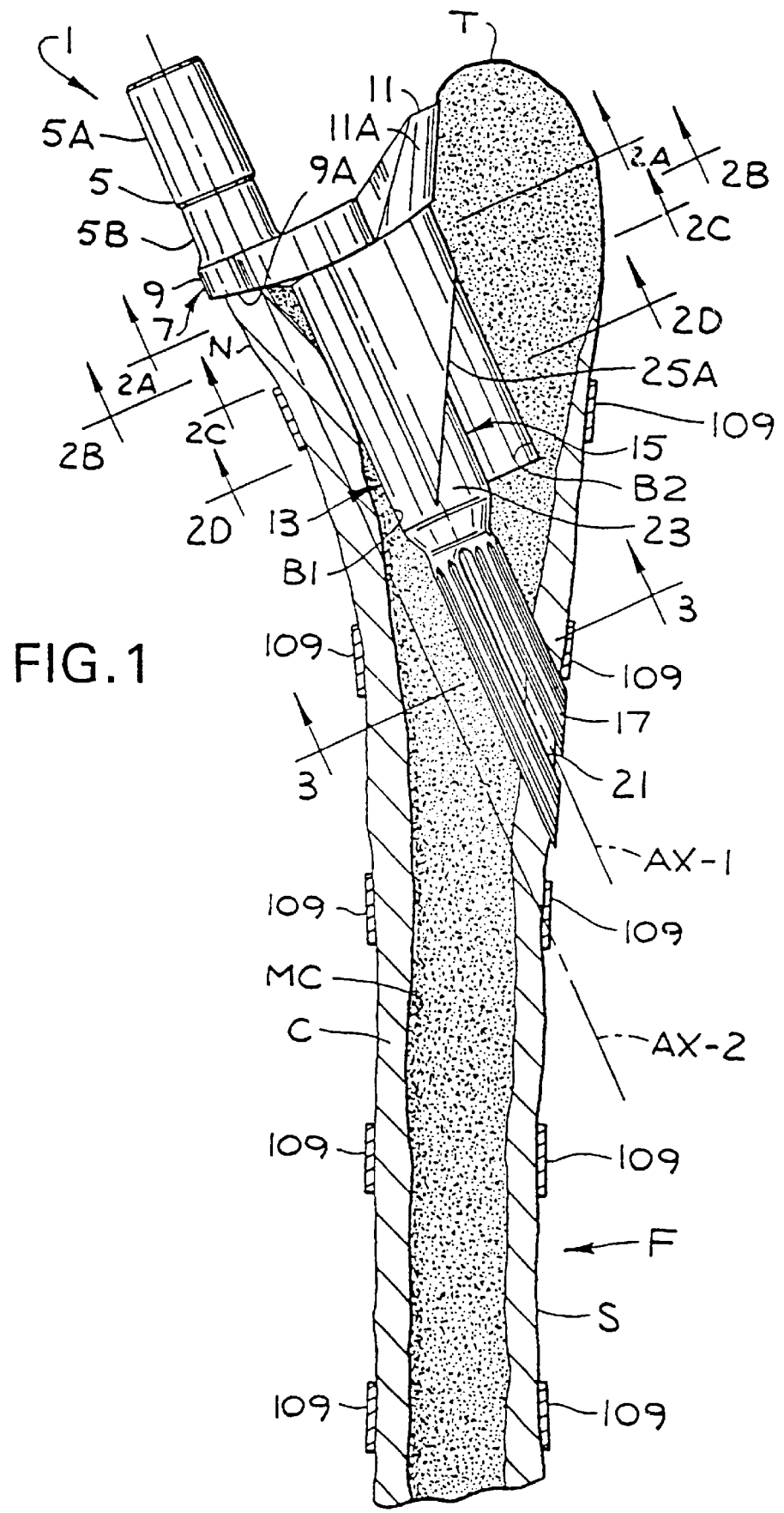
FIG. 1 is a fragmentary cross section of an upper femur showing a femoral head-neck prosthesis of the present invention implanted in the femur (the prosthesis being shown in full lines)
Figure 1A:
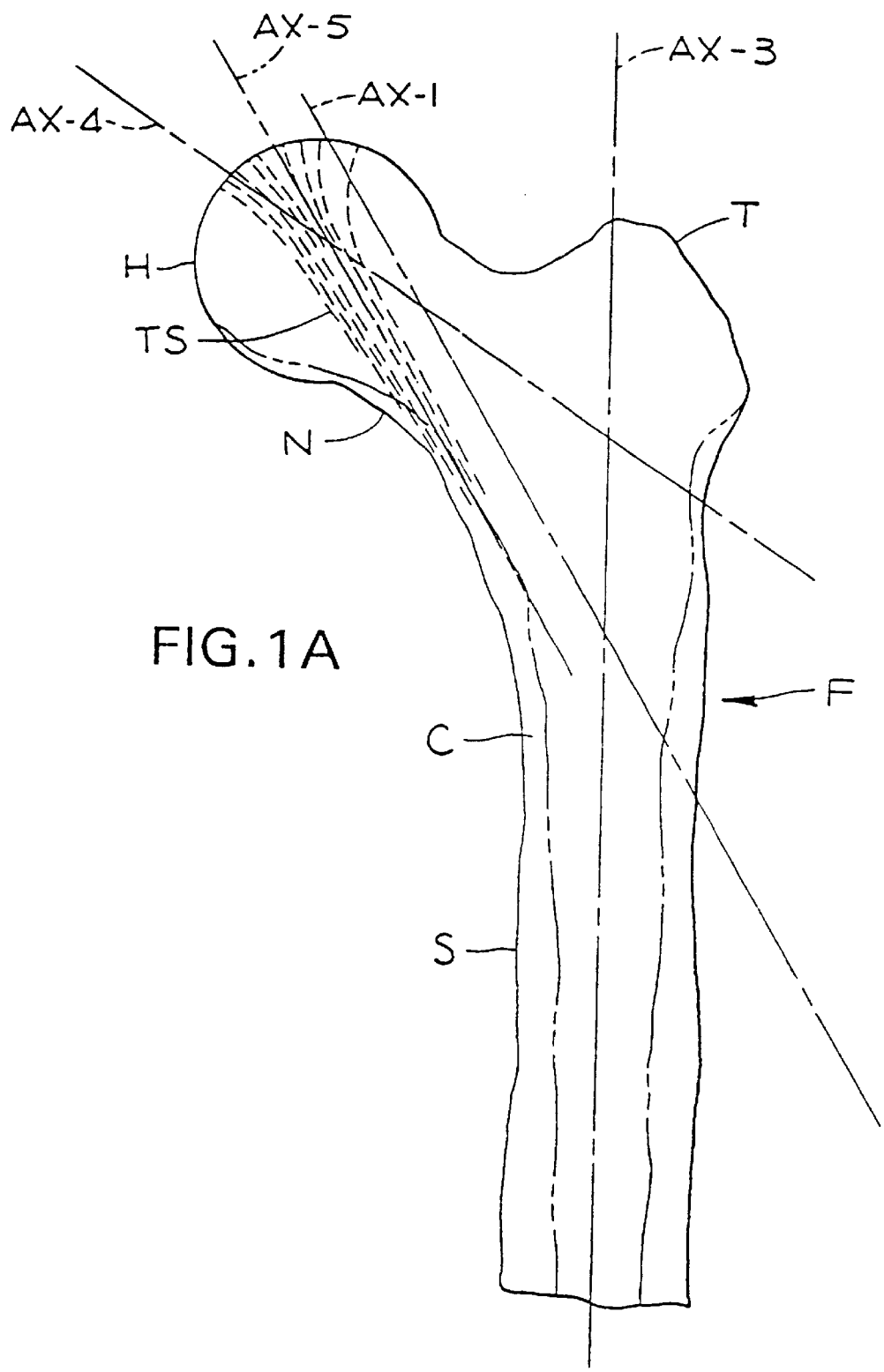
FIG. 1A is a view of an intact femur showing the medial trabecular stream of the femur and axes of the femur and prosthesis.
Figure 1B:
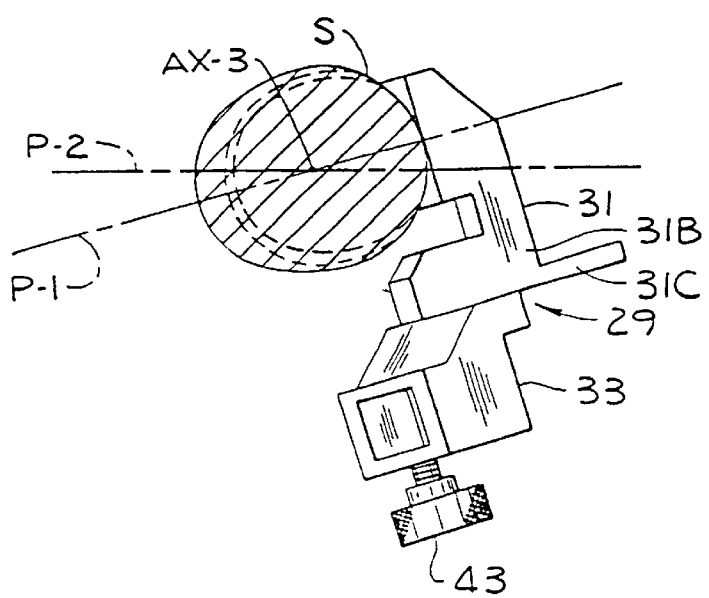
FIG. 1B is a cross-sectional view through the femoral neck illustrating the planes of the femur.

DETAILED DESCRIPTION OF THE PREFERRED EMBODIMENTS (a) The Femoral Head-Neck Prosthesis Referring now to the drawings, and in particular to FIGS. 1, 1A and 1B, a transosseous, non-cemented femoral head-neck prosthesis of the present invention (indicated generally at 1) is shown as implanted in a femur F. The femur includes a femoral shaft S, a femoral head H, neck N and a greater trochanter T at the upper end of the shaft at the lateral side of the femur. The femur F has a hard layer of cortical bone C adjacent the surface of the bone, relatively soft cancellous bone and endosteum (not shown) inside the femur. The prosthesis 1 is made of cobalt-chrome alloy, titanium or other suitable material, and has a longitudinal axis generally indicated at AX-1. As implanted, the prosthesis 1 extends generally from the resected femoral neck N diagonally across the medullary canal MC and out (posterolaterally) an opposite side of the femur. The prosthesis 1 is of the type which is not cemented into the femur F, but is secured by mechanical interconnection of the prosthesis with the bone, as described more fully hereinafter. The prosthesis 1 is constructed so that it is securely held in the bone from rotation (about its longitudinal axis AX-1) and toggling (anterior-posterior and medial-lateral) motion, while permitting axial micromotion to achieve natural bone loading condition thereby to preserve the bone.

The prosthesis 1 has a generally spherical ball 3 which is received in a cup (not shown) implanted in the hip socket (not shown) to permit movement at the hip joint. Referring now additionally to FIGS. 5A–5H, the ball 3 is fixedly attached to an upper portion 5A of a neck 5 of the prosthesis which is received in a hole (not shown) in the underside of the ball. The neck 5 is generally cylindrical in shape and includes a lower portion 5B below the upper portion 5A which is of a smaller diameter than the upper portion. The lower portion SB of the neck is mounted on a collar (generally indicated at 7) of the prosthesis 1 which rests against the femoral neck N, as shown in FIG. 1, and transmits loads to the upper femur. As shown, the collar 7 is continuous about the circumference of the prosthesis 1 and extends outward laterally, anteriorly, medially and posteriorly to cap the medullary canal MC. As shown, the collar 7 is continuous about the circumference of the prosthesis 1 and extends outward laterally, anteriorly, medially and posteriorly to cap the medullary canal MC.

The collar 7 includes a neck platform 9 on which the neck 5 is mounted, and a curved flange 11 which engages the greater trochanter T of the femur. The underside of the neck platform 9A has a slight frustoconical shape and the underside of the flange 11A has the shape of a section of cone. In the preferred embodiment, the underside 9A of the platform makes an angle of about 10° with a plane perpendicular to the longitudinal axis AX-1 of the prosthesis. The shape of the underside 9A and its close correspondence to the shape of the seat formed on the resected neck N allow the collar 7 to cap the medullary canal MC and inhibit migration of debris into the medullary canal after implantation of the prosthesis 1. The curved underside 11A of the flange makes an angle of about 60° with the same plane. Thus, the underside (9A, 11A) of the collar 7 defines a compound angle. The flatter neck platform 9 lies on the partially resected femoral neck N, and the flange 11 rests against the greater trochanter T of the femur. The greater trochanter is the primary sight of muscle attachment to the femur F at the hip. The upstanding flange 11 permits the collar 7 to solidly support the prosthesis 1 on cortical bone C on the upper femur while allowing most of the greater trochanter T to be preserved. Use of a substantially flat collar (not shown) would require resection of a substantial portion of the trochanter T to provide room for the collar. The underside (9A, 11A) of the collar 7 of the present invention engages and is supported by the hard cortical bone C of the femur.

In the preferred embodiment, the underside 9A of the neck platform 9 and underside 11A of the flange 11 are coated with a porous material (not shown) to facilitate bone growth into the collar 7 where it rests on the upper end of the femur F. However, the remaining portions of the collar 7 and all other parts the prosthesis 1 preferably remain free of porous coating, roughening or other construction which would encourage bone growth into the prosthesis. It is to be understood that the use of porous coating or other structure to facilitate bone ingrowth into the prosthesis 1 may be other than described and still fall within the scope of the present invention.

A stem, generally indicated at 13, mounted on the underside of the collar 7 extends generally downwardly through the femur F. In the preferred embodiment, the neck 5, collar 7 and stem 13 are formed as one piece. The longitudinal axis AX-2 of the neck 5 is parallel to the longitudinal axis of the stem, which is coincident with the longitudinal axis AX-1 of the prosthesis 1. As installed, the prosthesis 1 is substantially parallel to an axis AX-5 (FIG. 1A) corresponding to the direction of the normal loading vector of the hip so that forces from the hip are applied compressively to the neck 5 which transmits those forces (via the collar 7) compressively to the femoral neck N. Axial fixation of the prosthesis 1 in the bone is achieved by bone ingrowth of the upper femur F into the collar 7. As described more fully hereinafter, axial fixation of the stem 13, caused by bone ingrowth into the stem and/or strain hardening of bone engaging the stem, is prevented by construction of the stem.

Figure 3:
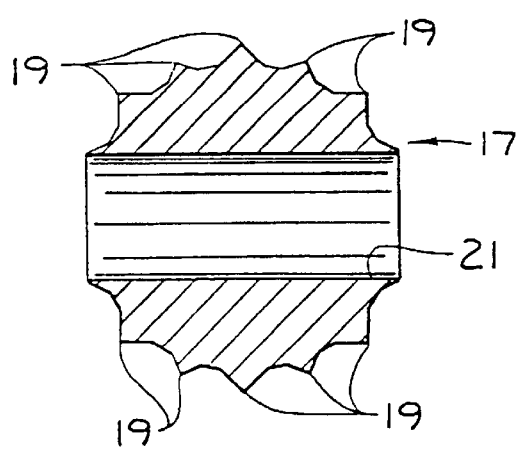
FIG. 3 is a cross-section through the splined portion of the lower stem taken in the plane of line 3—3 of FIG. 1.
Figure 2A:
FIGS. 2A–2D illustrate areas of contact between the upper prosthesis and bone at locations indicated by lines 2A—2A through 2D—2D, respectively.
Figure 2B:
Figure 2C:
Figure 2D:
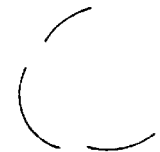

The stem 13 includes an upper portion and a lower portion (designated generally by reference numerals 15 and 17, respectively). The radially outwardly facing surfaces of the stem 13 disposed for engaging the interior of the femur F are, broadly, "fixation surfaces." The lower portion 17 is sized for a close fit within the femur F, and has longitudinally extending splines 19 (see FIGS. 3 and 5H) which penetrate the bone inside the femur to secure the prosthesis 1 in the femur. The lower portion 17 has a longitudinal split 21 to accommodate normal load deflection of the proximal femur. The splines 19 hold the prosthesis 1 securely against rotational movement about the longitudinal axis AX-1 of the prosthesis after implantation, and encourage bone growth between the splines. However, although the splines 19 resist axial displacement of the prosthesis 1 relative to the femur F, the splines do not rigidly fix the prosthesis against axial micromotion. To provide additional fixation of the prosthesis 1, splines (not shown) may also be formed on the upper portion 15 of the stem.

Figure 6:
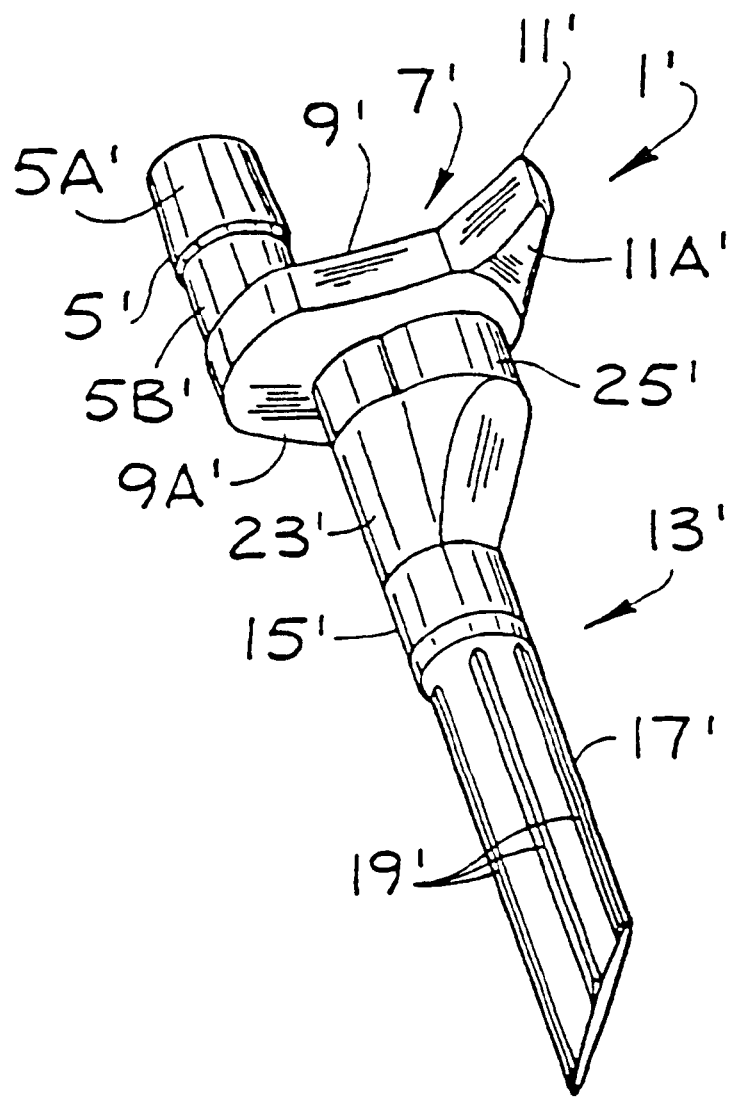
FIG. 6 is a perspective view of a solid stem prosthesis.
Figure 18B:
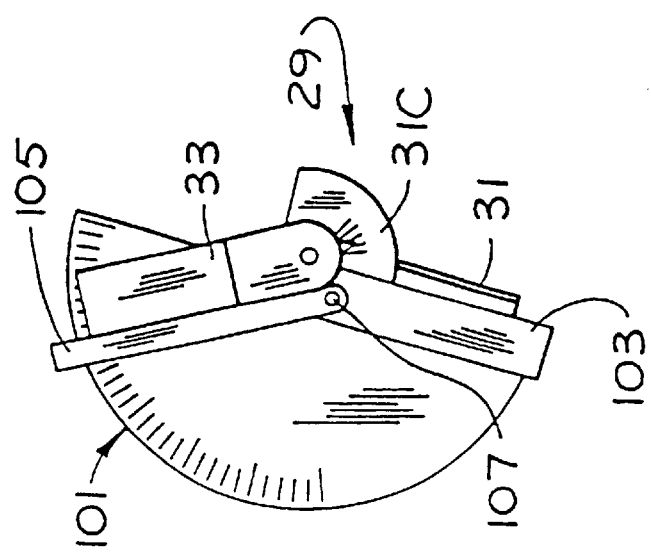
FIG. 18B is a view showing setting of the angle guide prior to mounting on the femur.

A more preferred embodiment of a prosthesis 1' is shown in FIG. 6 has a solid lower stem portion 17'. It is believed that the solid stem provides for greater accuracy in installation and prevents axial fixation which potentially might occur through ingrowth of bone into the slot 21 of the prosthesis 1. A still more preferred embodiment of a prosthesis 1" is shown in FIGS. 18P and 19 to have a flat underside 9A" of the collar 7".

The distal end of the lower portion 17 of the stem 13 is cut on an angle to the longitudinal axis, so that the distal end of the lower portion is somewhat pointed. Moreover, the distal end of the lower portion 17 is generally aligned with or parallel to the outer surface of the femur F on the posterolateral side. The lower portion 17 preferably extends outwardly from the posterolateral side of the femur F to inhibit bone growth over the distal end of the lower portion which would fix the prosthesis 1 in an axial direction and prevent the natural loading at the upper end of the femur by the collar 7.

The upper portion 15 of the stem 13 generally has the shape of overlapping cylinders near the collar 7 (see FIG. 5G). A first overlapping cylindrical element of the upper portion is designated 23, and a second overlapping cylindrical element of the upper portion is designated 25. The first (smaller) cylindrical element 23 is co-axial with the longitudinal axis AX-1 of the prosthesis 1, while the second (larger) cylindrical element 25 has an axis which is parallel to the first cylindrical element and radially offset a distance from the axis AX-1 less than the sum of the radii of the first and second cylindrical elements. The first cylindrical element 23 has a diameter greater than the coaxial stem lower portion 17 of the stem. The diameter of the lower portion 17 is kept small to minimize the size of the opening formed in the posterolateral femoral cortex. As an example, if the diameter of the first element 23 were 15 mm, the diameter of the lower portion 17 would be about 12 mm. The shape of the upper portion 15 is defined by the portions of the first and second cylindrical elements 23, 25 which are not overlapping. The offset, eccentric location of the second element 25 causes the upper portion 15, as received in the bores 3B, B2 to hold the prosthesis against rotation about axis AX-1. A lower end surface 25A of the second cylindrical element is cut in a plane which makes an angle of approximately 30° with respect to the longitudinal axis AX-1.

As illustrated by FIGS. 2A–D, the upper portion 15 of the stem 13 contacts the endosteal neck cortex of the femur F only in discrete areas around the circumference of the upper portion. The cross sectional views of the drawings (taken as indicated in FIG. 1) schematically illustrate the regions of engagement of the cortex and the upper portion 15 of the stem at four distinct locations along the length of the upper portion. It will be noted that engagement does occur at three spaced apart locations around the upper portion 15 so that the upper portion is able to provide good fixation against both rotation motion of the prosthesis 1 about its longitudinal axis AX-1 and toggling motion of the prosthesis about axes perpendicular to the longitudinal axis.

However, the discrete areas of contact do not rigidly fix the upper portion 15 of the stem 13 against axial movement relative to the femur F. The limited area of contact reduces the frictional interaction of the prosthesis 1 and bone in the endosteal neck cortex. Moreover, the upper stem portion 15 has smooth exterior walls which substantially prevent bone from growing into the upper stem portion thereby to prevent axial fixation of the prosthesis by bone ingrowth. Thus, the upper stem portion 15 will not prevent loads from the hip from being applied compressively to the upper end of the femur F. This more natural loading of the femur induces more natural straining of the upper femur and prevents deterioration of the upper femur, which is important to maximizing the useful life of the implanted prosthesis 1.

(b) Instruments used to Implant the Prosthesis

Figure 7A:
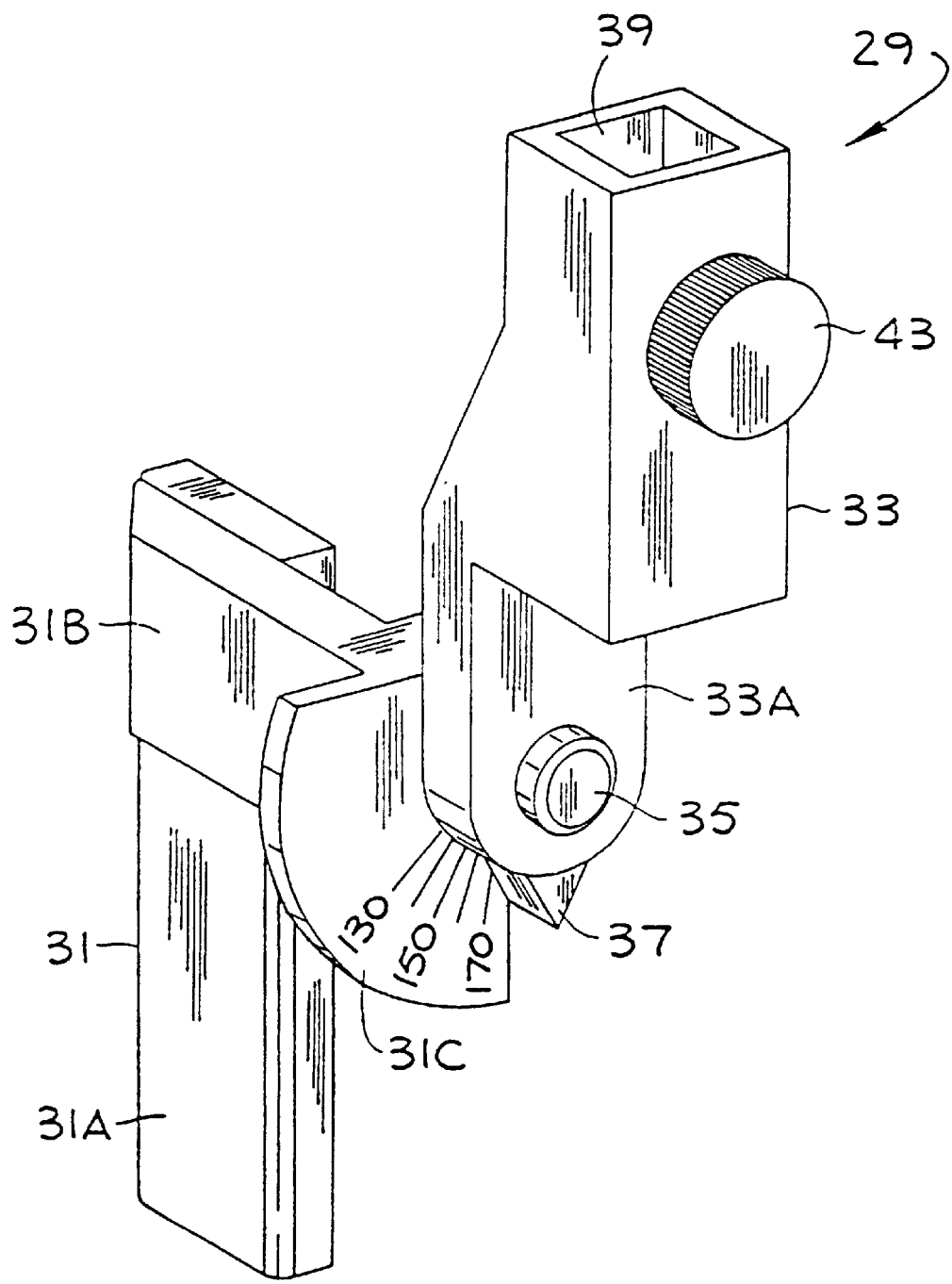
FIG. 7A is a perspective view of an angle guide.
Figure 8A:
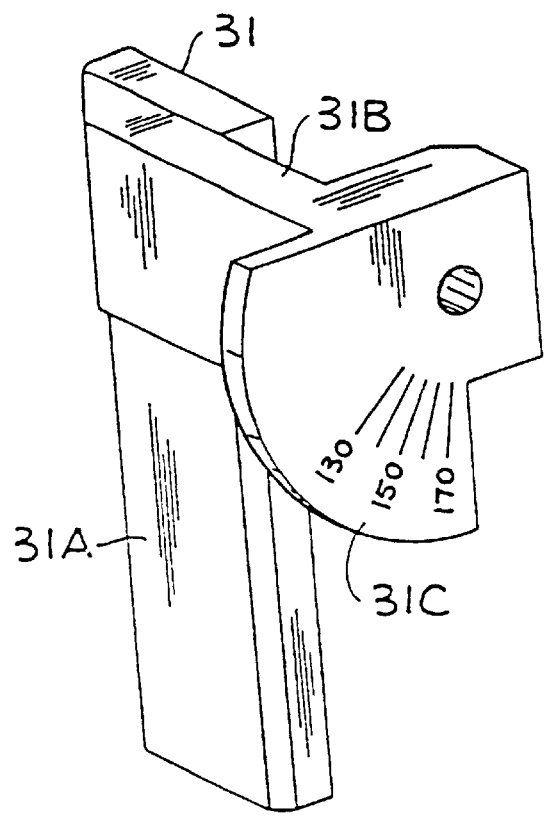
FIG. 8A is a perspective view of a bracket of an angle guide.
Figure 8B:
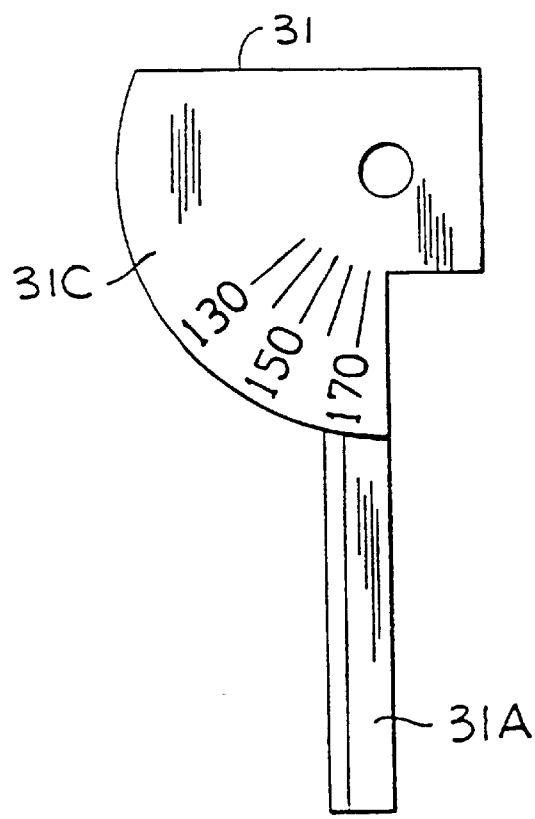
FIG. 8B is a front elevational view thereof.
Figure 8C:
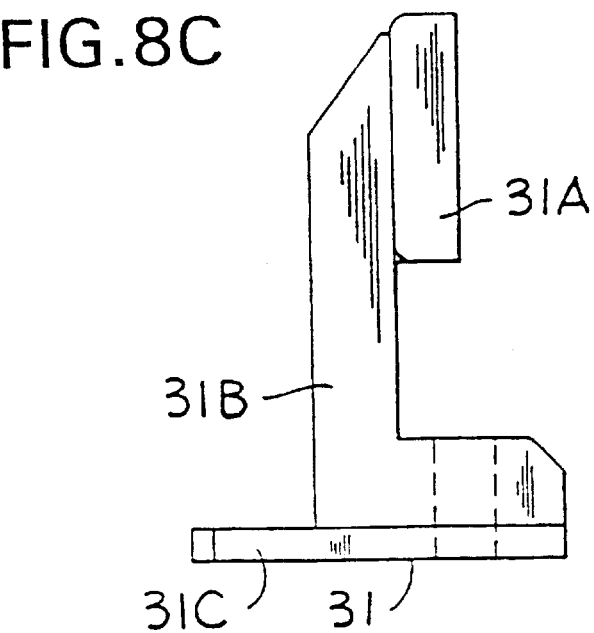
FIG. 8C is a top plan view of a bracket thereof.
Figure 8D:
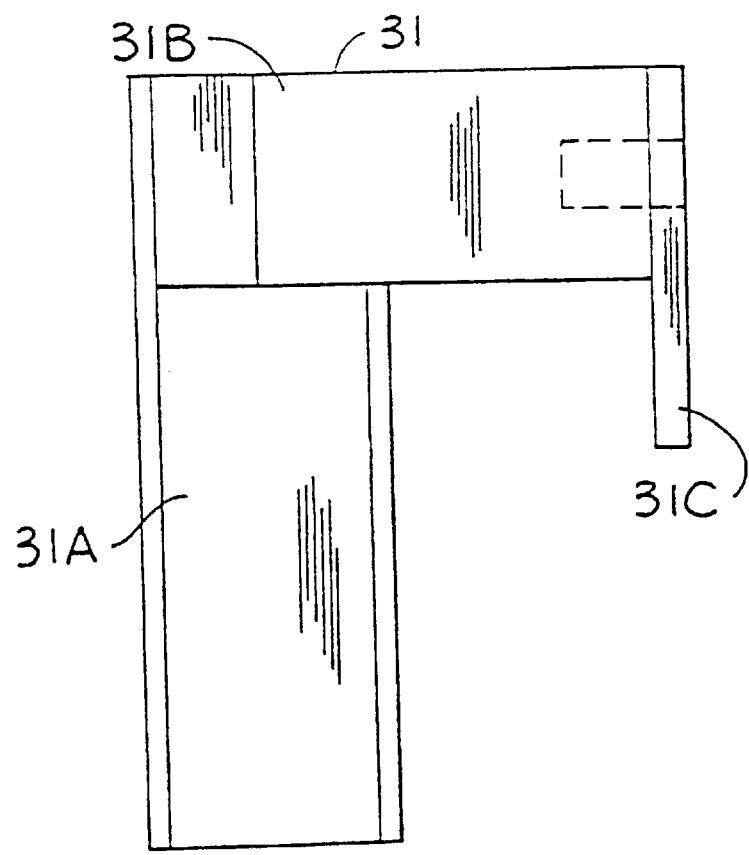
FIG. 8D is a left side elevational view thereof.
Figure 9A:
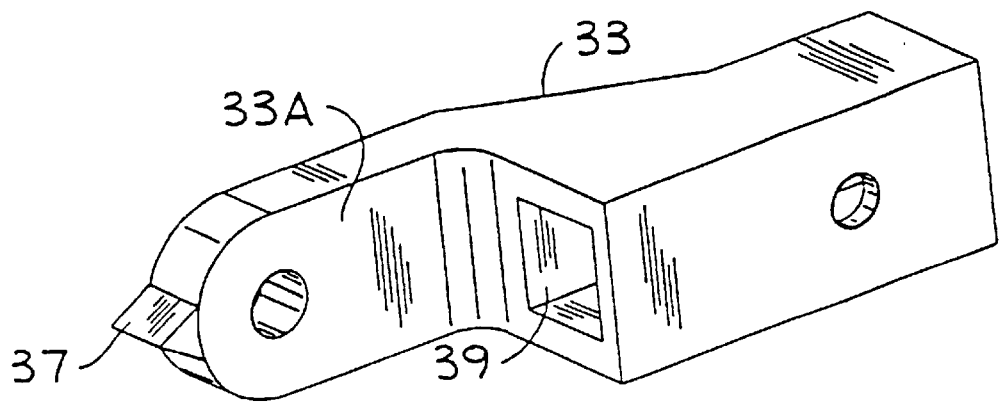
FIG. 9A is a perspective view of an arm of the angle guide.
Figure 9B:
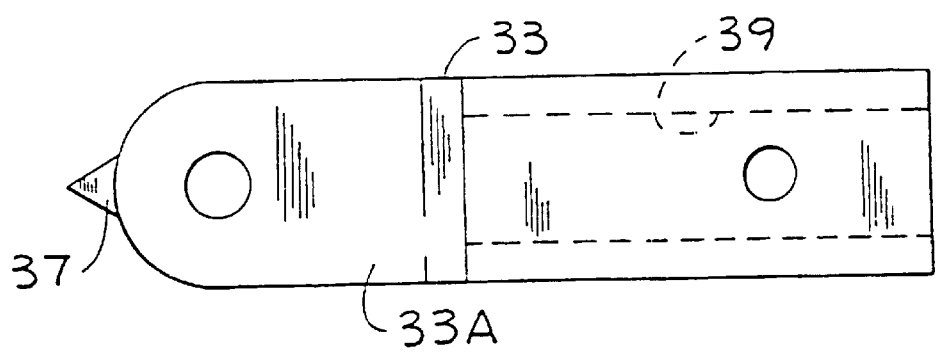
FIG. 9B is a front elevational view thereof.
Figure 9C:
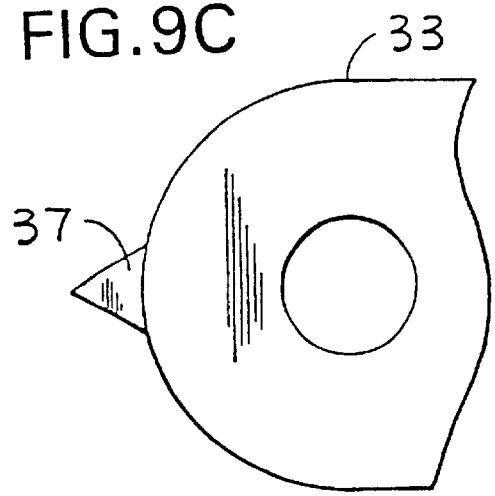
FIG. 9C is an enlarged, fragmentary front elevational view of the left end of the arm.
Figure 9D:
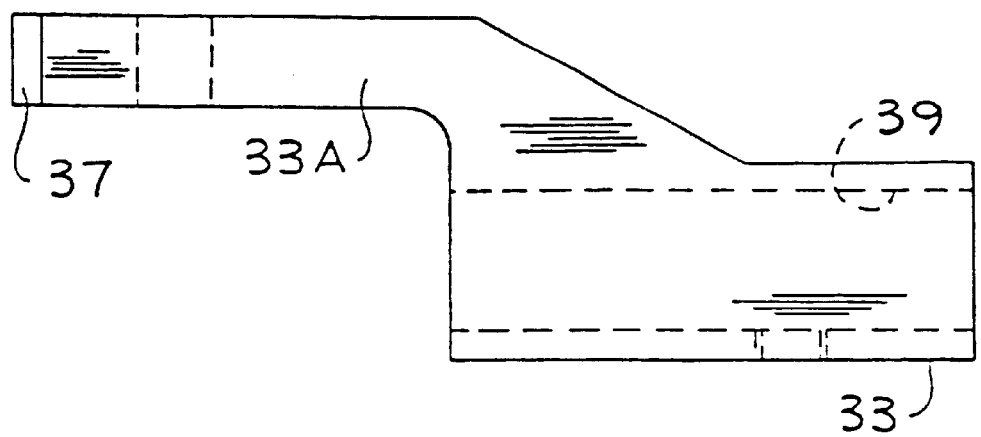
FIG. 9D is a top plan view of the arm of the angle guide.
Figure 9E:
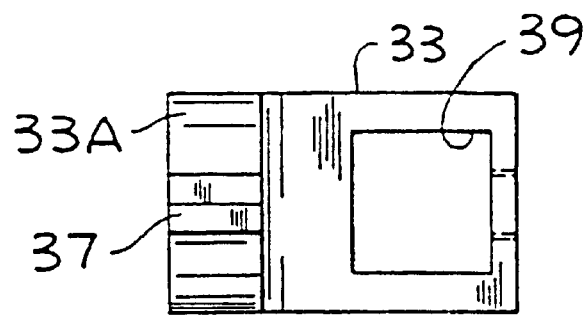
FIG. 9E is a left side elevational view thereof.
Figure 10A:
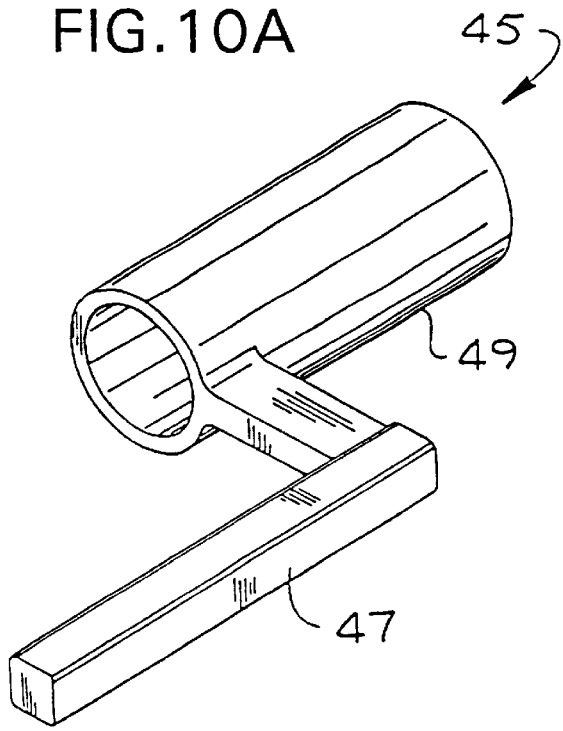
FIG. 10A is perspective view of a calcar miller guide.
Figure 10B:
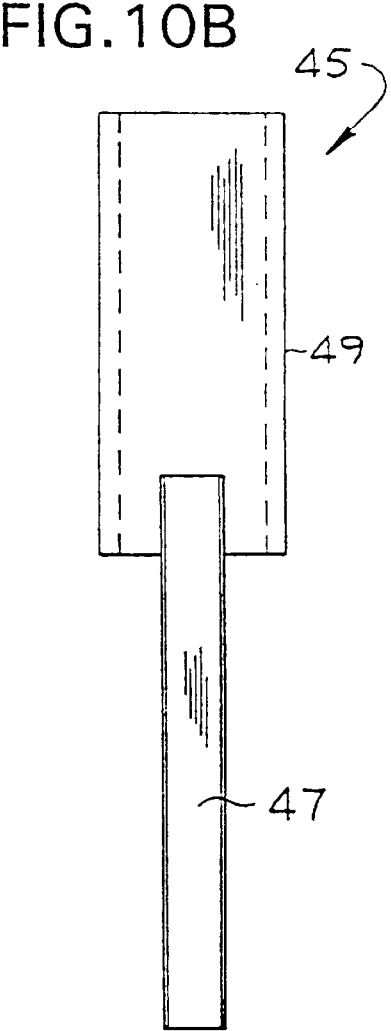
FIG. 10B is a front elevational view thereof.
Figure 10C:
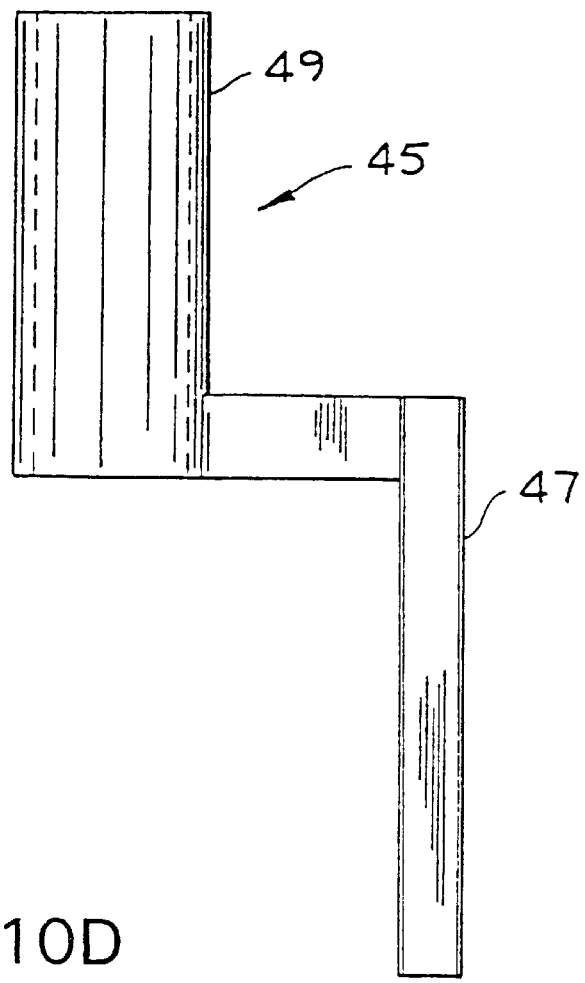
FIG. 10C is a front elevational view thereof.
Figure 10D:
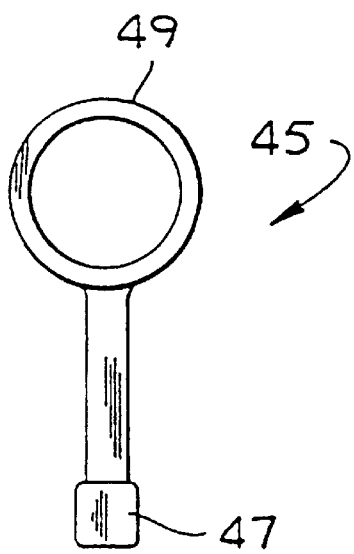
FIG. 10D is a bottom plan view thereof.
Figure 11A:
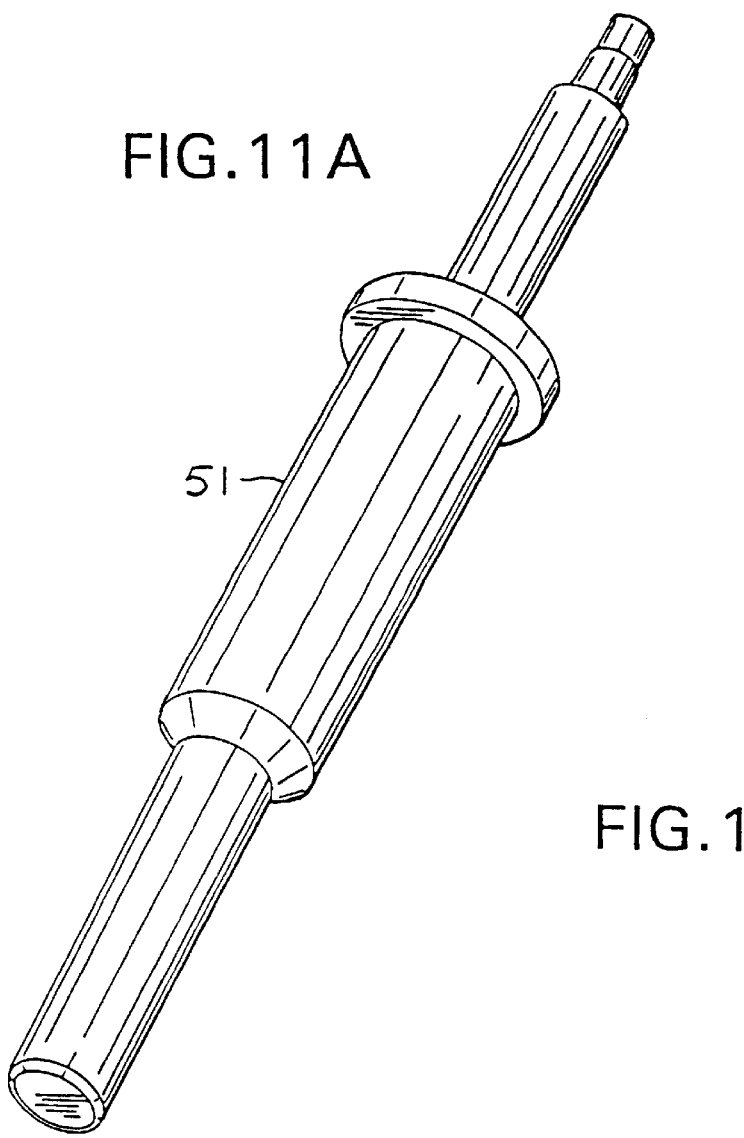
FIG. 11A is a perspective view of a calcar miller.
Figure 11B:
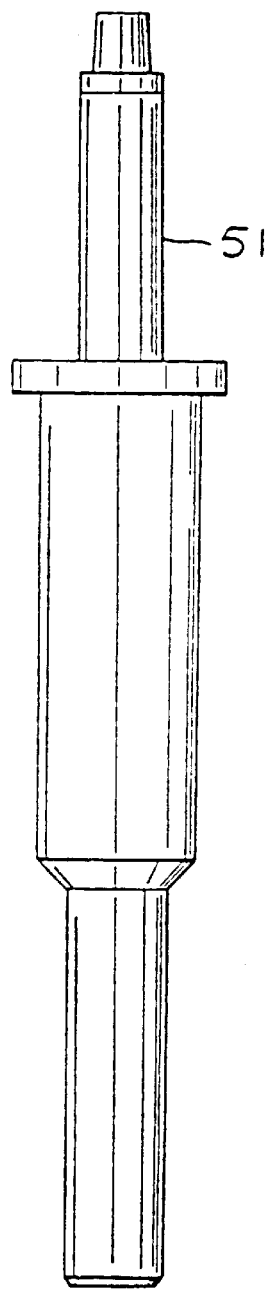
FIG. 11B is an elevational view of the calcar miller.
Figure 11C:
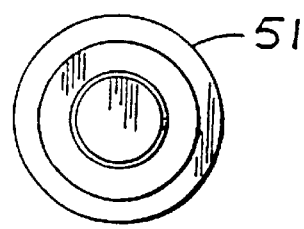
FIG. 11C is a bottom end view of the calcar miller.
Figure 12A:
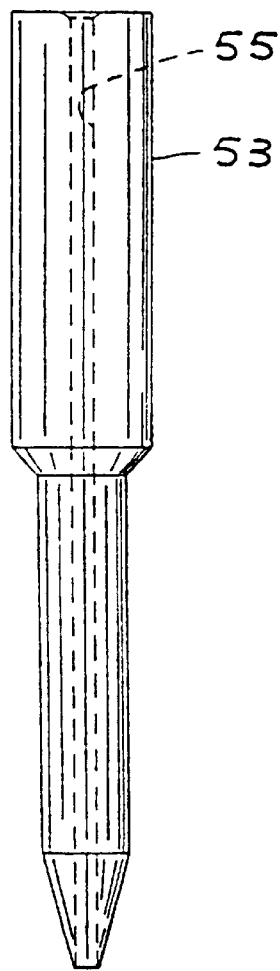
FIG. 12A is an elevational view of a cannulated pin guide.
Figure 12B:
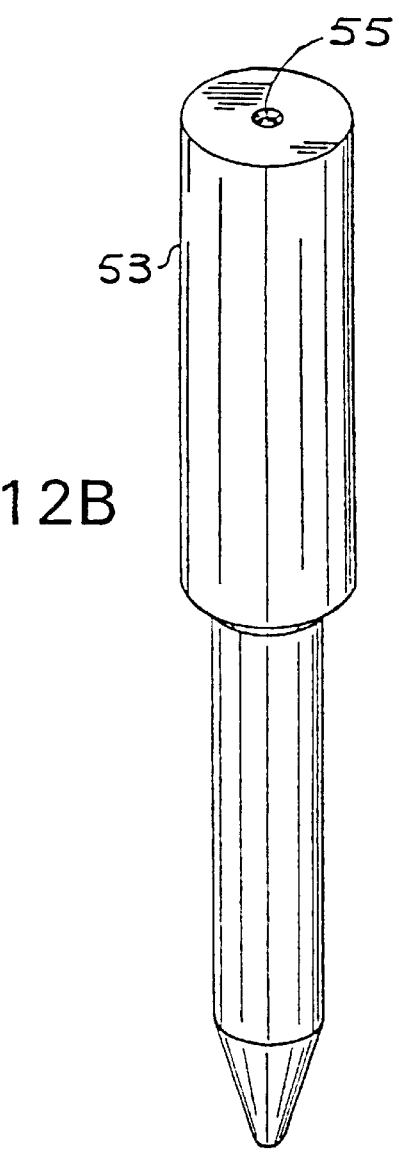
FIG. 12B is a perspective view of the cannulated pin guide.
Figure 12C:
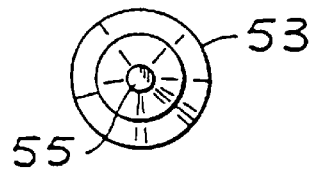
FIG. 12C is a bottom end view thereof.
Figure 12D:
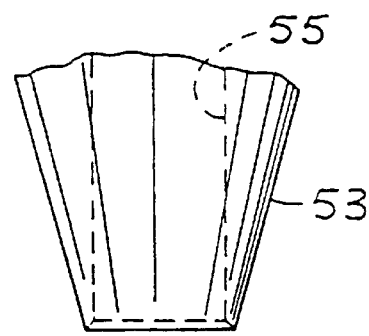
FIG. 12D is a fragmentary, elevational view of the cannulated pin guide showing the bottom end.
Figure 13A:
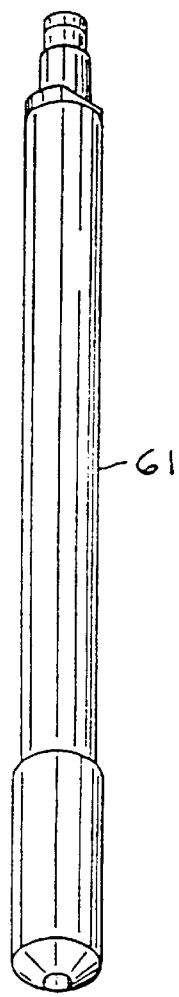
FIG. 13A is a perspective view of the cannulated cortex drill.
Figure 13B:
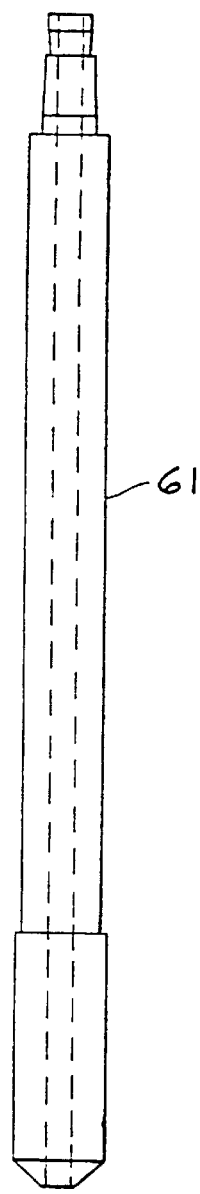
FIG. 13B is a front elevational view of a cannulated cortex drill.
Figure 13C:
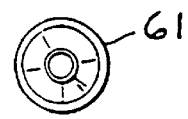
FIG. 13C is a bottom end view thereof.
Figure 13D:
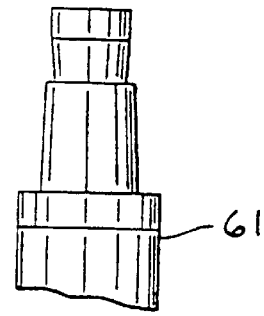
FIG. 13D is a fragmentary front elevational view of a top end of the cannulated cortex drill.

While a number of different instruments may be helpful for implanting the femoral head-neck prosthesis 1, an angle guide generally designated at 29 and shown in FIGS. 7A–7C is particularly adapted to be removably secured to the femoral shaft S for holding a plurality of cutting, drilling and reaming accessories in position with respect to the femur F. The angle guide 29 comprises a bracket 31 (see FIGS. 8A–8D) having a first member 31A adapted to be removably secured by a suitable clamp (not shown) in face-to-face engagement with the femoral shaft S. A second member 31B extends outwardly from the first member 31A and includes an arcuate faceplate 31C. A guide sleeve 33 or outrigger portion (see FIGS. 9A–9E) is capable of extending at a selected angle upwardly and outwardly from the bracket 31 at one side of the femoral shaft. The guide sleeve 33 includes a mounting member 33A attached to the bracket 31 by a screw 35. The guide sleeve 33 may be angularly adjusted relative to the bracket 31 by loosening the screw 35 and turning the guide sleeve on the screw to a selected angular position. The faceplate 31C carries indicia which are pointed to by a pointer 37 associated with the mounting member 33A to show the angle of the guide sleeve. The angle is selected so that the guide sleeve 33 extends from the bracket 31 along a line substantially parallel to the previously determined average compression loading vector (the "normal" direction in which the femur F is loaded, AX-5) for the femur of the specific patient when the bracket is attached to the Femur.

The guide sleeve 33 has a through hole 39 for receiving and holding other instruments in the same angular position as the guide sleeve.

As noted above, angle guide 29 is adapted for holding a variety of different instruments used in implanting the prosthesis 1 of the present invention. One such instrument is a saw guide 41 (see FIG. 4B) which can be detachably mounted in the through hole 39 of the guide sleeve 33 for guiding a saw blade (not shown) to cut the femoral neck N. The saw guide 41 has a sawcut slot 41A generally perpendicular to the central longitudinal axis of guide sleeve 33. The saw guide 41 is slidably adjustable in the through hole 39 to properly position it with respect to the femoral neck N. A set screw 43 of the angle guide 29 is provided for securing the saw guide 41 in adjusted position.

Referring now to FIGS. 10A–11D a calcar miller guide, generally indicated at 45, has an outrigger portion 47 receivable in the through hole 39 of the angle guide 29 for mounting on the angle guide in the same manner as the saw guide 41. The calcar miller guide has a guide tube 49 attached to the outrigger portion 47. Calcar miller guide 45 is slidably adjustable along guide sleeve 33 in the through hole 39 to properly position it with respect to the femoral neck seat of the femoral neck N. The calcar miller guide 45 is fixedly held from rotation with respect to the guide sleeve 33. The position of the calcar miller guide tube 49 over the femoral neck N defines the axis AX-1.

A number of calcar millers (not shown) are provided having progressively larger diameters to gradually increase the side of the hole formed in the femur F. A final calcar miller 51 (FIGS. 11A–11C) is sized to mill the first bore 21 in the medial endosteum to provide a close fit between the prosthesis 1 and the medial endosteum.

A cannulated pin guide 53 (FIGS. 12A–12D) is sized to be received through the guide tube 49 of the calcar miller guide 45 and to be slidably received in the first bore B1 created by a calcar miller 51 in the femoral neck N. The cannulated pin guide 53 has a central axial passage 55 to slidably receive a trocar point guide pin 57 (FIG. 4N) and a drill point guide pin 59 (FIG. 4P). The trocar point guide pin 57 and the drill point guide pin 59 have the same diameter, e.g., 3.5 mm.

A cannulated cortex drill 61 (FIGS. 13A–13D) is sized to be slidably received over the drill point guide pin 59. The cannulated cortex drill 61 is sized to drill a bore through the posterolateral femoral cortex C that is slightly smaller in diameter than the distal stem of the prosthesis 1 (e.g., 9 mm for a 9.5 mm diameter prosthesis stem).

Figure 14A:
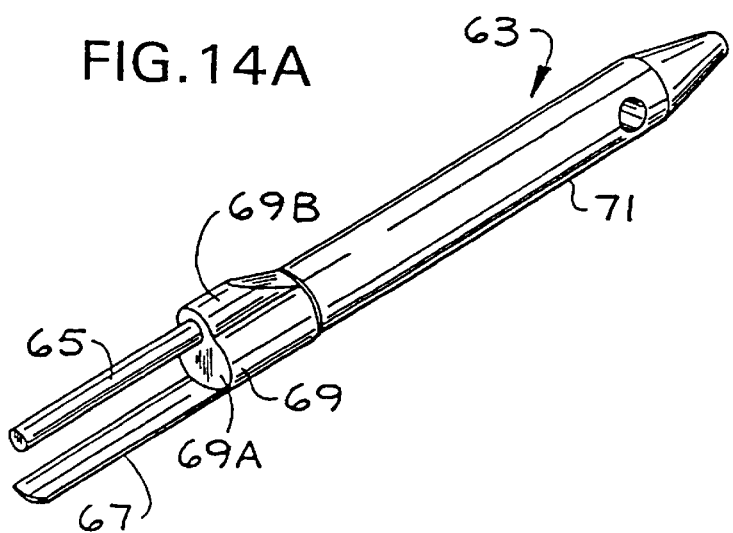
FIG. 14A is a front view of the offset reaming guide.
Figure 14B:
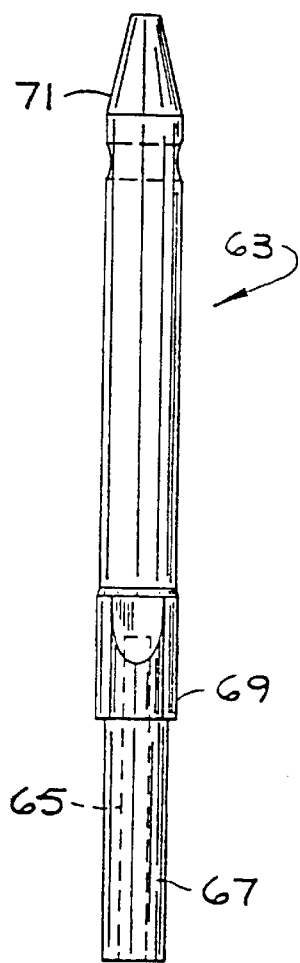
FIG. 14B is a front elevational view thereof.
Figure 14D:
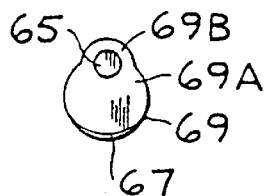
FIG. 14D is a top plan view of the offset reaming guide.
Figure 14E:
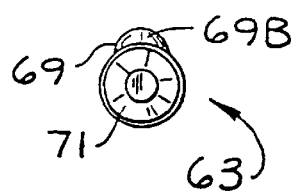
FIG. 14E is a bottom plan view of the offset reaming guide.
Figure 14C:
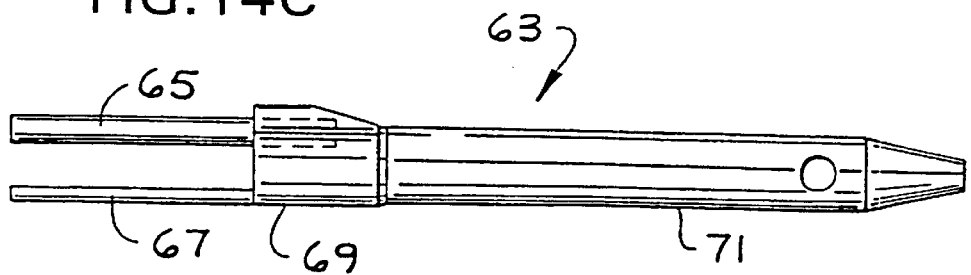
FIG. 14C is a left side elevational view thereof.
Figure 15A:
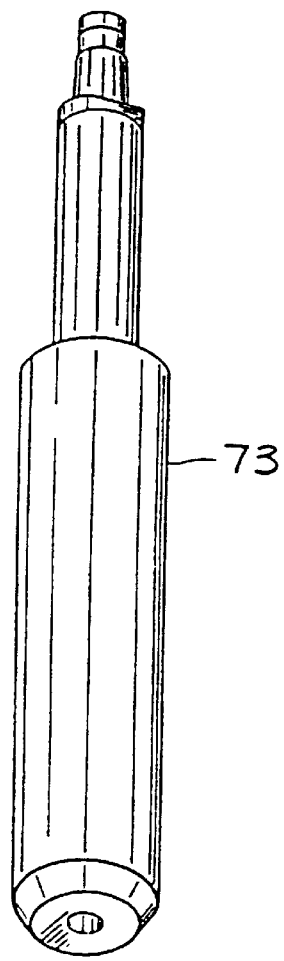
FIG. 15A is a perspective view of the cannulated reamer.
Figure 15B:
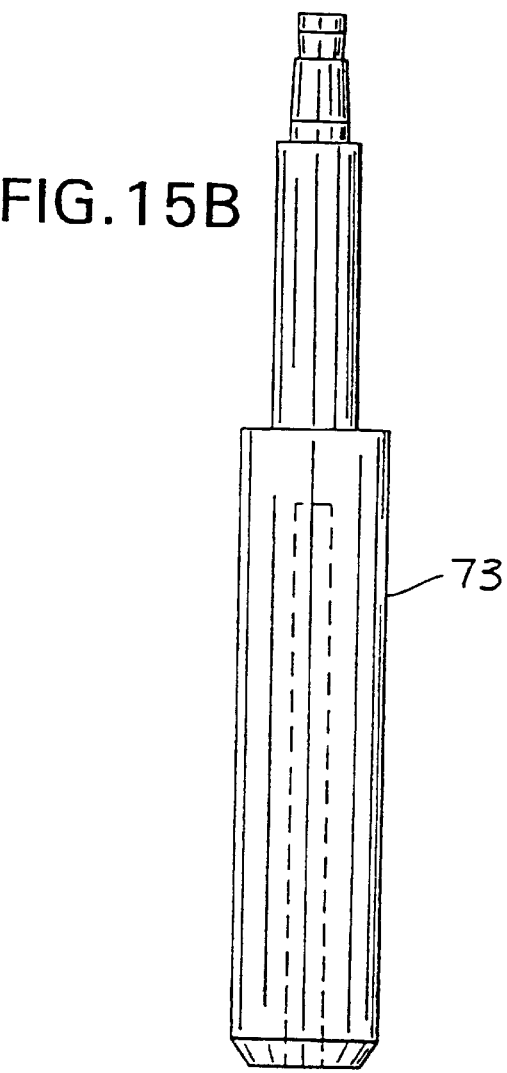
FIG. 15B is an elevational view of a cannulated reamer.
Figure 15C:
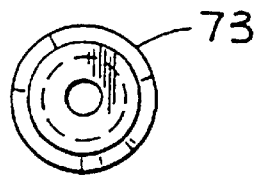
FIG. 15C is a bottom end view of the cannulated reamer.
Figure 15D:
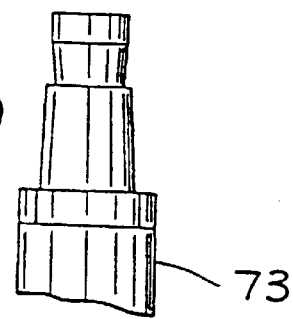
FIG. 15D is an enlarged, fragmentary elevational view of the cannulated reamer showing an upper end.

An offset reaming guide, generally indicated at 63 (FIGS. 14A–14E), is sized to be slidably received in the first bore B1. The offset reaming guide 63 comprises a trunnion 65 and guide finger 67 mounted on a platform 69, and a distal end section 71. The distal end section 71 of the offset reaming guide 63 is sized (14 mm in the illustrated embodiment) to allow passage through the first bore B1 and has a bullet distal end to facilitate passage through the first bore. The exterior shape of the platform 69 (as seen from the ends of the reaming guide 63) is generally that of non-overlapping surfaces of two axially parallel, radially overlapping cylinders (see FIGS. 14C and 14E). A larger cylinder 69A of the overlapping cylinders coaxial with the axis of the distal end section 71 of the reaming guide 63 is larger than that of a smaller cylinder 69B. The smaller cylinder 69B is cut on a plane angling downwardly toward the intersection with the larger cylinder 69A. The largest transverse dimension of the platform 69 is about 15 mm to provide line-to-line fit with the first bore B1. However, it is to be understood that the transverse dimension of the platform will vary depending upon the size of the bone.

The guide finger 67 is disposed parallel to and generally in registration with the trunnion 65. The guide finger 67 engages the endosteal wall in the femur F to facilitate holding the trunnion 65 in position as a cannulated reamer 73 (see FIGS. 15A–15D) cuts the bone. The trunnion 65 is cylindrical and offset about 6 mm from the central longitudinal axis of the distal end section 71 of the offset reaming guide 63. The precise offset distance will vary depending upon the size of the bone in which the prosthesis 1 will be installed. The trunnion 65 is sized to receive the cannulated reamer 73 thereon and to permit rotation of the cannulated reamer on the trunnion for reaming the bone while guiding the reamer along a line parallel to the axis AX-1 of the first bore B1 formed in the femur F. The cannulated reamer 73 forms the second bore B2.

A calcar planing guide, generally indicated at 75, comprises a stem 77 including an upper portion 77A and a lower portion 77B, and a trunnion 79 generally coaxial with the stem (FIGS. 16A–16D). The calcar planing guide 75 has a bullet shaped distal tip to aid in passage through the first bore B1. The shape of the stem 77 is generally the same as that of the prosthesis 1 except that the lower stem portion 77B is smooth (i.e., lacking the splines 19 of the prosthesis). The upper portion 77A of the stem is received in a double bore (first B1 and second B2) arrangement formed in the femur neck. The calcar planing guide 75 fits snugly in the first and second bores B1, B2 to hold the planing guide from moving within the femur F. The exterior surface of the stem 77 is smooth in the embodiment illustrated in FIGS. 16A and 16B.

Figure 16D:
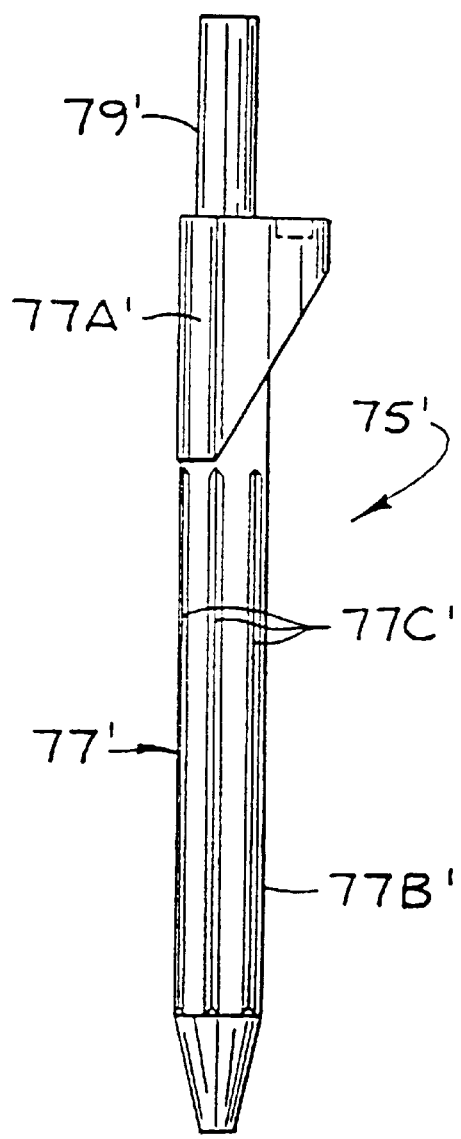
FIG. 16D is a front elevational view of a calcar planing guide of a second embodiment.
Figure 16C:
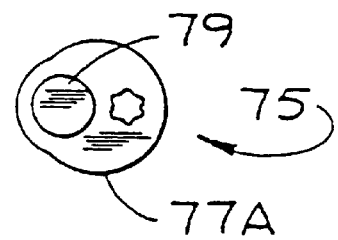
FIG. 16C is a top plan view of the calcar planing guide.

However, the calcar planing guide should preferably correspond closely to the shape of the prosthesis 1. FIG. 16D illustrates an embodiment of a calcar planing guide 75' in which the stem 77' has solines 77C' corresponding identically to the splines 19 of the prosthesis. In the event the prosthesis 1 also had splines (not shown) on the upper portion 15 of its stem 13, similar splines (not shown) would be formed on the upper portion 77A' of the planer guide stem 77'. By more precisely matching the shapes of the stems (13, 77') of the prosthesis 1 and planing guide 75', a greater congruency of the underside (9A, 11A) of the collar 7 and the seat formed on the neck N may be achieved.

Figure 17A:
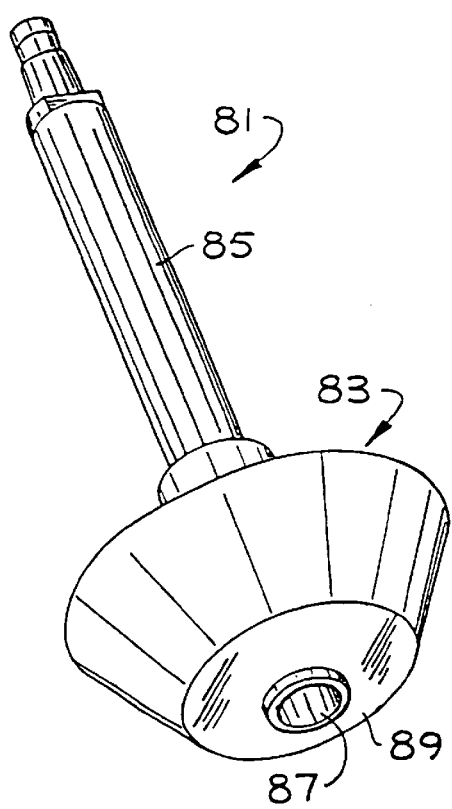
FIG. 17A is a perspective view thereof.
Figure 17B:
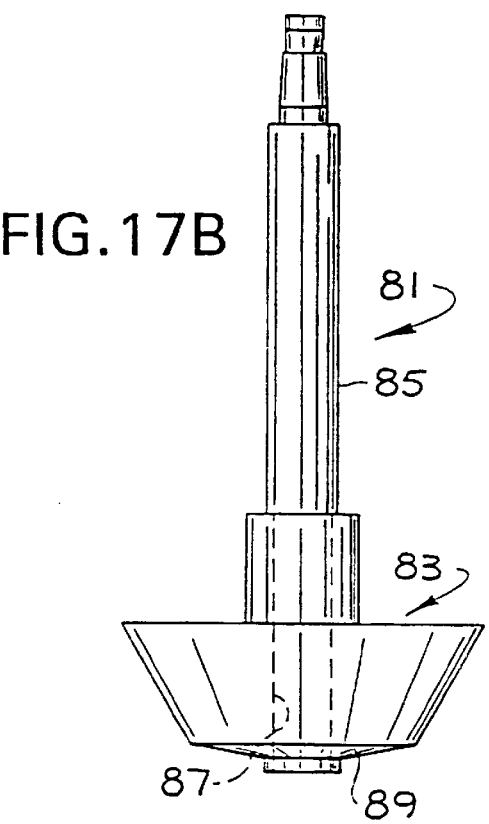
FIG. 17B is a front elevational view of a calcar planer.
Figure 17C:
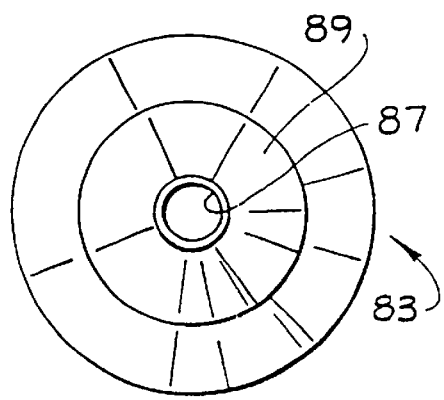
FIG. 17C is a bottom end view thereof.

A calcar planer of the present invention (generally indicated at 81) forms a seat for the collar 7 of the prosthesis 1 on the resected neck N of the femur F (see FIGS. 17A–17C). The calcar planer 81 comprises a head, generally indicated at 83, and a shaft 85 extending axially from the head. The calcar planer head has a central axial passage 87 which receives the trunnion 79 of the planing guide 75 therein to mount the planer on the planing guide for rotation relative to the planing guide on the trunnion. The bottom 89 of the head 83 has the shape of a frustum of a cone. The angle of the cone to a plane perpendicular to the central longitudinal axis AX-1 is about 100 when the planer 81 is mounted on the planer guide 75. The side 91 of the head 83 is also conical in shape, making an angle of about 60° with the plane perpendicular to the central longitudinal axis AX-1. The shape of the head 83 corresponds closely to the shape of the underside (9A, 11A) of the collar 7.

In the event the prosthesis 1" having a flat underside 9A" is to be installed, the bottom 89' of the head 83' of the calcar planer 81' is also flat. The calcar planer 81' having a flat bottom 89' is illustrated in FIG. 18M. It is believed the use of the flat bottomed calcar planer 81' and prosthesis 1" increases the chance of obtaining a very high level of congruency between the prosthesis and the seat on the neck N formed by the calcar planer.

(c) Method of Implanting the Prosthesis

Figure 18A:
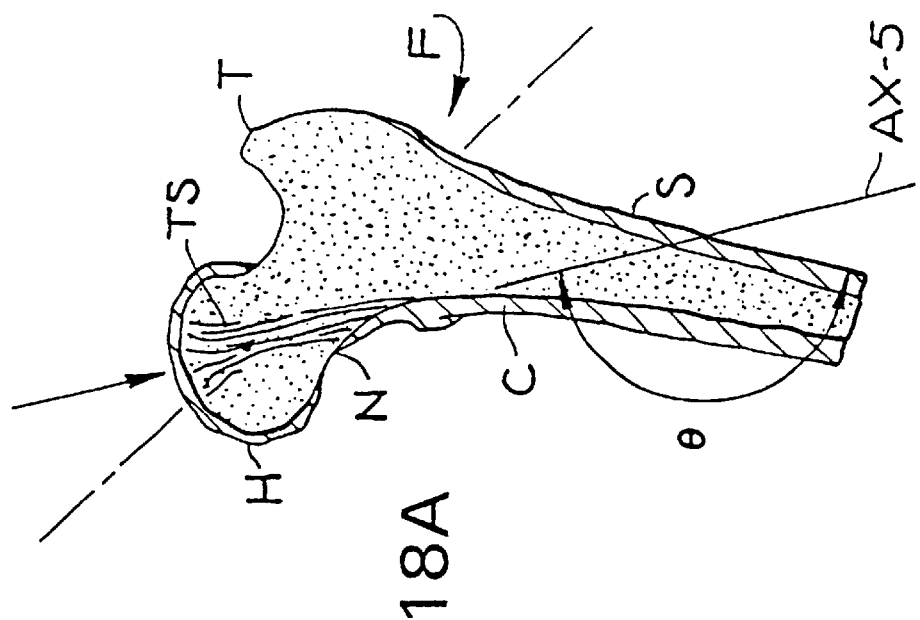

The method of the present invention for implanting the prosthesis 1 assures close replication of normal loading of the femur F (i.e., loading prior to implantation of the prosthesis). One preferred method of the present invention is illustrated in FIGS. 4A, 4B and 4M–4S. A lesser preferred method is illustrated in FIGS. 4A–4L. A most preferred method is illustrated in FIGS. 18A–18P. A femoral head-neck prosthesis which fails to replicate normal loading conditions will change the stress distribution through the femur F. As mentioned in U.S. Pat. No. 4,998,937, incorporated herein by reference, according to Wolff's law these changes in stress distribution eventually cause alterations in the internal structure of the bone. Those portions subject to a lesser stress than before are likely to deteriorate and those subject to greater stress than before are likely to thicken. Excessive increases in stress over those associated with normal loading may kill the bone cells if the stress is applied over an extended period of time. To replicate normal loading, the method of the present invention aligns the stem 13 of the prosthesis 1 with the average compression loading vector for the particular femur, which vector is variable from person to person.

Referring to FIG. 1A, the human femur F has two externally visible axes: the axis of the femoral neck AX-4 and the axis of the femoral shaft AX-3. However, the bone is not loaded along either of these two visible axes, but rather is loaded through a third axis (parallel to the average compression loading vector) which is not externally apparent. In response to compressive loading and the strain energy density experienced by the femur F, reinforcing lines of bone, which are called compression trabeculae, form within the femur. The collection of these reinforcing lines is the compression trabecular stream TS. The particular collection of compression trabeculae in the femur neck, as shown in FIG. 1A, is referred to as the medial trabecular stream TS, and the average direction of the medial trabecular stream may be referred to as the medial trabecular stream axis AX-5. Angle θ which axis AX-5 makes with the central longitudinal axis of the femur shaft AX-3 generally ranges from 140 to 170 degrees. In practice, this angle is measured from a profile X-ray of the hip between the axis AX-5 and a lateral surface of the femur F (see FIG. 4A). The use of the medial trabecular stream TS to position the prosthesis 1 is discussed in U.S. Pat. No. 4,998,937.

To install the prosthesis 1 in the femur F in accordance with the method of this invention, the hip joint and the lateral side of the femur are first surgically exposed. A vertical plane P-1 through the central longitudinal axis AX-2 of the femoral neck is typically at an angle of approximately 15 degrees anterior to a lateral-medial plane P-2 through the central longitudinal axis AX-3 of the femoral shaft, as shown in FIG. 1B. This angle is commonly referred to as the "anteversion" of the femoral neck. Accordingly, the angle guide 29 is positioned radially on the femur F such that the vertical axis of bracket 31 lies in plane P-1 approximately 15 degrees posterior from the lateral-medial plane P-2 (since the bracket is lateral of axis AX-3 and the femoral neck 7 is medial). In this position, a vertical plane P-3 through guide sleeve 33 should be parallel to plane P-1. In addition, the angle guide 29 is positioned proximally-distally on the femur F such that the upper end of guide sleeve 33 is centered with respect to the base of the femoral neck, as shown in FIG. 1B. The angle guide 29 is then clamped on the femoral shaft S by a clamp (not shown). The guide sleeve 33 is adjusted, by loosening screw 35, relative to the bracket 31 so that its angle relative to the central axis AX-3 of the femur shaft S matches the angle e of the medial trabecular stream TS. This is accomplished by aligning pointer 37 of the guide sleeve with the appropriate angle indicated on the faceplate 31C of the bracket 31.

Figure 4B:
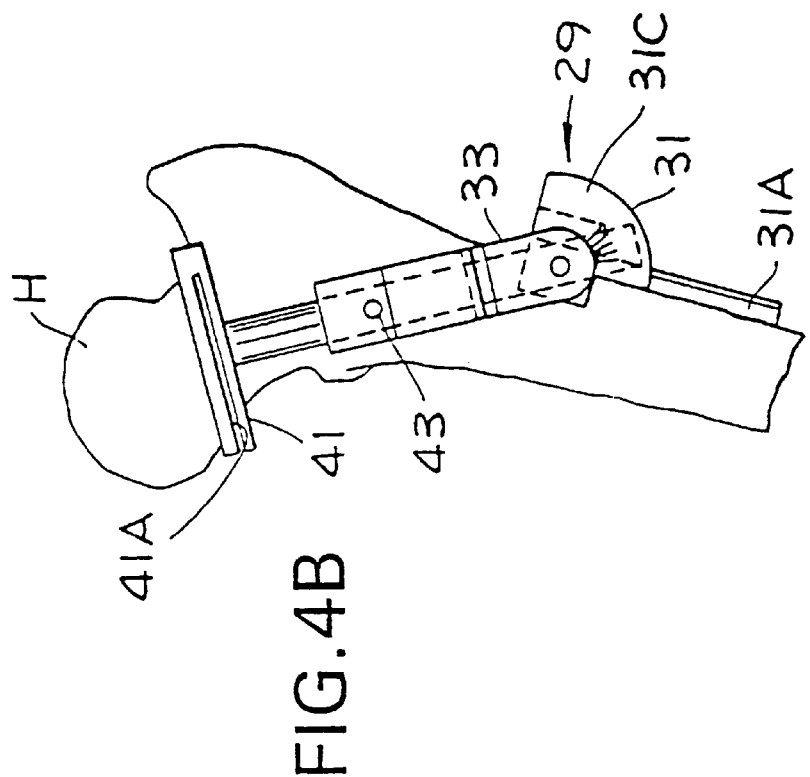
FIG. 4B is a view showing the angle guide and the saw guide around the femur for femoral neck resection.
Figure 4A:
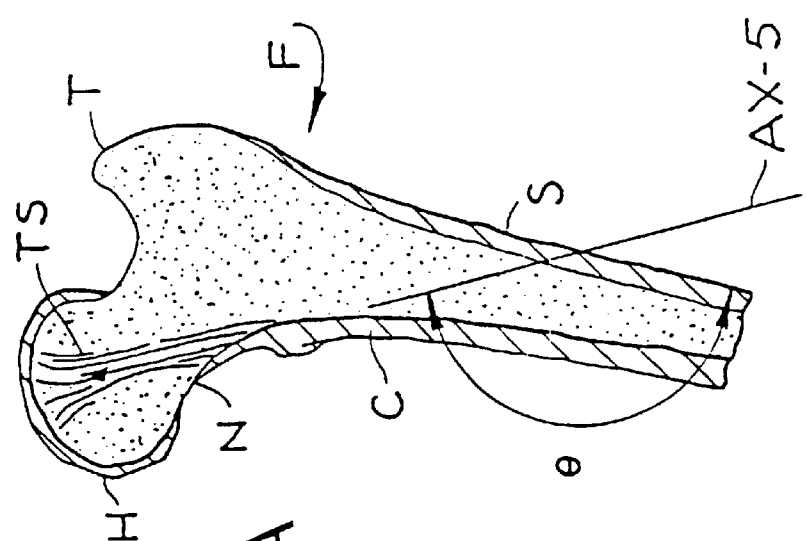
FIGS. 4A–R are schematic views of a lesser preferred embodiment and a preferred embodiment of a method of implanting the prosthesis.
Figure 4D:
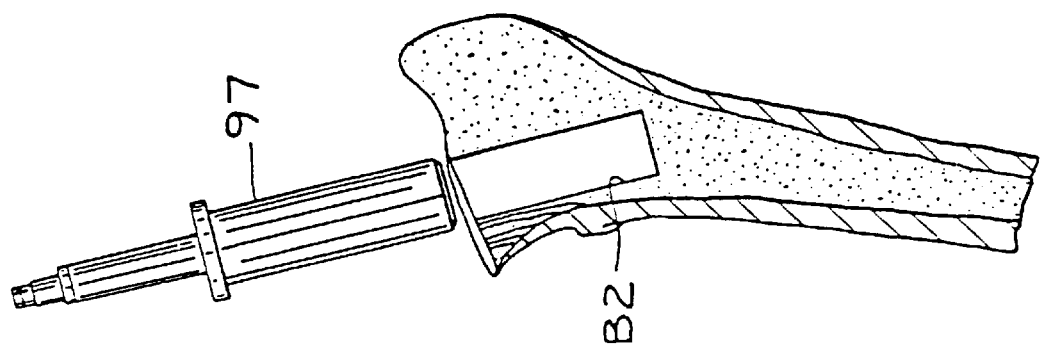
FIG. 4D is a view showing the reamer for reaming the second bore in the femoral neck.
Figure 4C:
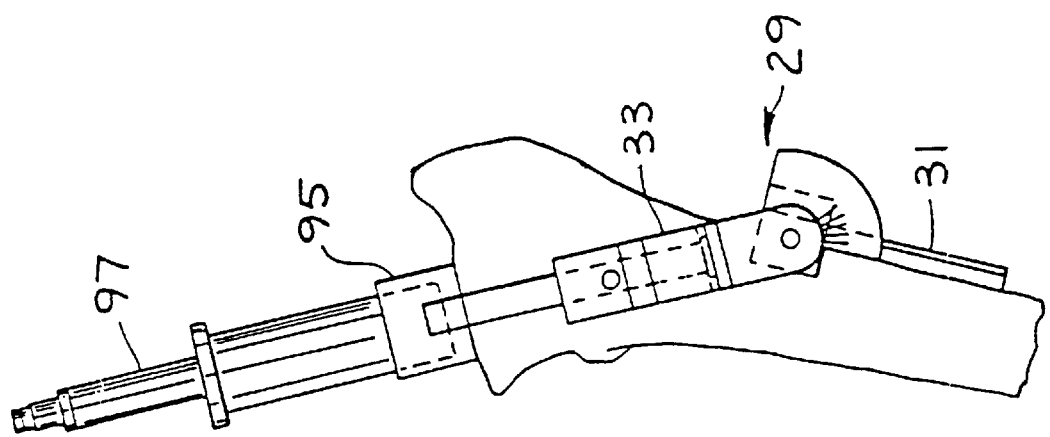
FIG. 4C is a view showing the angle guide, a reamer guide and a reamer for reaming of the second bore in the femoral neck.

The saw guide 41 is positioned (proximally-distally) on guide sleeve 33 such that the sawcut slot 41A is located adjacent the base of the femoral neck N and generally aligned with the upper surface of the lateral femoral cortex of the femur F, as shown in FIG. 4B. In this position, the sawcut slot should be perpendicular to the medial trabecular stream TS. Set screw 43 is tightened to firmly attach the saw guide 41 in the guide sleeve 33 of the angle guide 29.

With the saw guide 41 in place, the femoral neck N is cut with an oscillating saw (not shown) by passing the saw through the sawcut slot 41A to form a cut surface extending from the lateral femoral cortex at an angle of approximately 60 degrees with respect to the central longitudinal axis AX-3 of the femur shaft S. The saw guide 41 is then removed from the guide sleeve 33, leaving the angle guide 29 attached to the femoral shaft S in its original position, and the femoral head H is removed.

If a total hip replacement (i.e., replacement of the femoral head H and acetabulum (not shown) is required, the acetabulum should now be prepared.

In the first preferred embodiment, as shown in FIGS. 4A, 4B and 4M–4S, the calcar miller guide 45 is secured to the guide sleeve 33, which effectively centers the calcar miller guide with respect to the cut surface of the femoral neck N. The angle guide 29 also aligns the calcar miller guide 45 parallel to the axis AX-5. A starter hole is drilled into the femoral neck 7.

A miller (not shown) of relatively small milling diameter is slidably received in he calcar miller guide 45 to mill the femoral neck. The femoral neck N is milled by a progression of end and side cutting millers, with each succeeding miller having a larger diameter than the preceding miller. The femoral neck N has an inner lining (or surface) referred to as the endosteum. The final milling diameter is determined for the individual femur to provide an appropriate diameter of the first bore B1 adjacent to the medial endosteum. The calcar miller 51 of the appropriate diameter mills a bore in the medial endosteum to the final diameter (e.g., 15 mm). The calcar miller 51 is then removed from the calcar miller guide 45 (FIG. 4M).

Figure 4F:
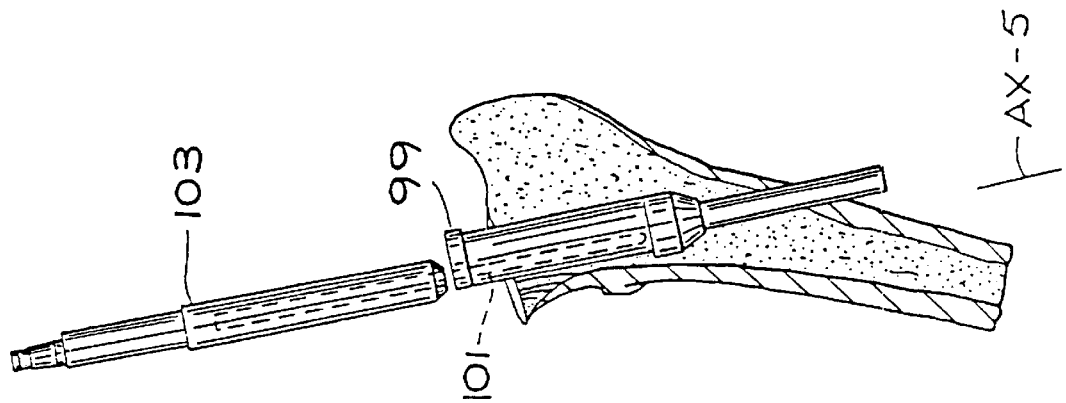
FIG. 4F is a view showing the calcar milling guide and calcar miller for milling the first bore in the femoral neck with the angle guide omitted for clarity.
Figure 4E:
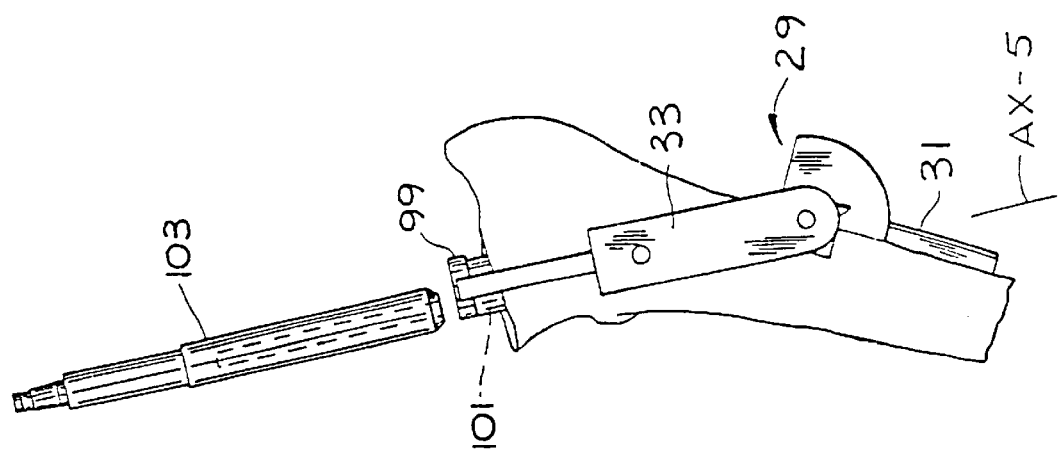
FIG. 4E is a view showing the angle guide, calcar milling guide and calcar miller for milling the first bore in the femoral neck.
Figure 4H:
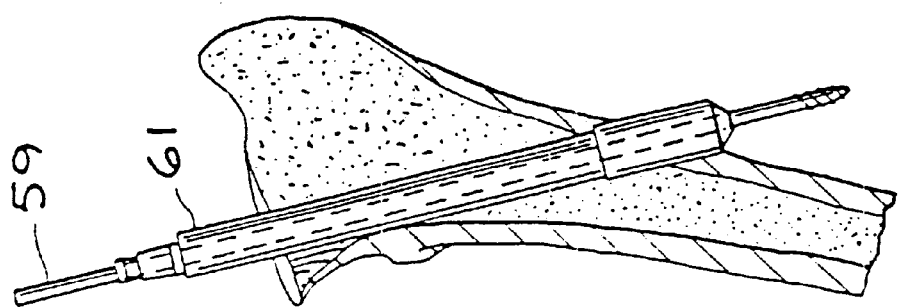
FIG. 4H is a view showing the drill point guide pin and a cannulated cortex drill for drilling through the lateral femoral cortex.
Figure 4G:
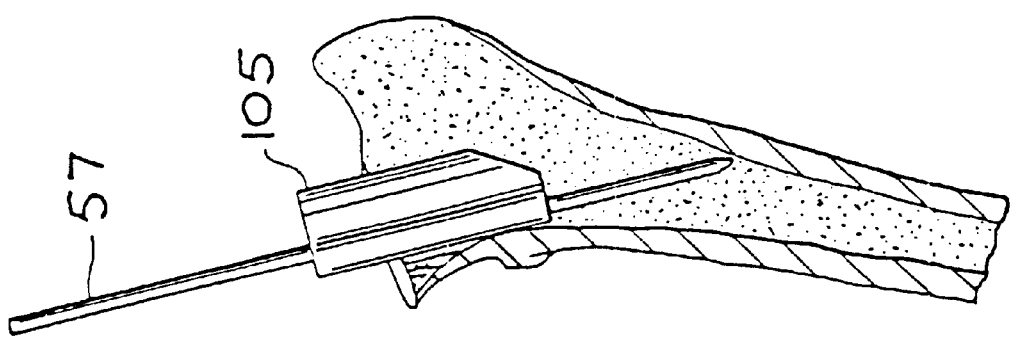
FIG. 4G is a view showing a drill pin guide, a trocar point guide pin and a drill point guide pin for drilling through the lateral femoral cortex.
Figure 4M:
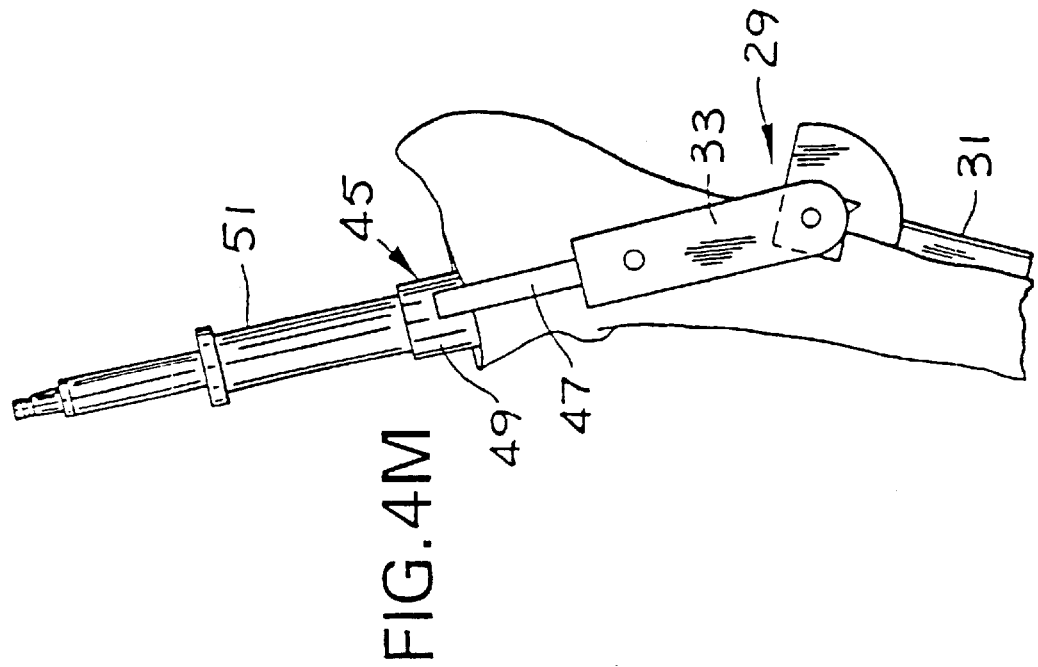
FIG. 4M shows the start of the more preferred implantation steps and is a view showing the calcar miller for milling the first bore.
Figure 4L:
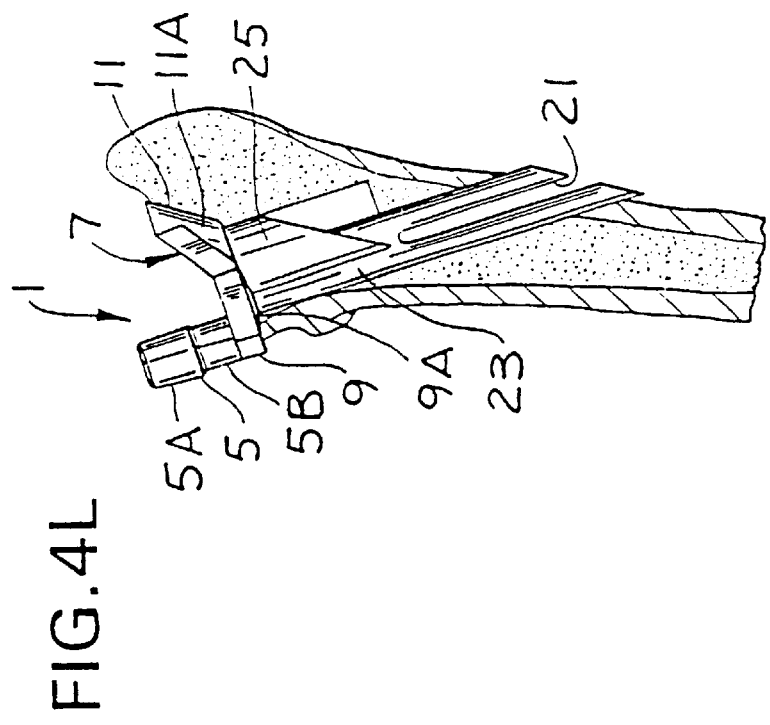
FIG. 4L is a view showing the implantation of the prosthesis.
Figure 4P:
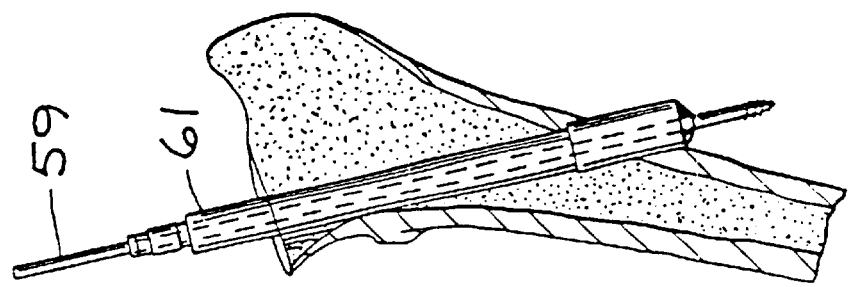
FIG. 4P is a view showing the drill point guide pin and cannulated cortex drill for drilling through the posterolateral femoral cortex.
Figure 4N:
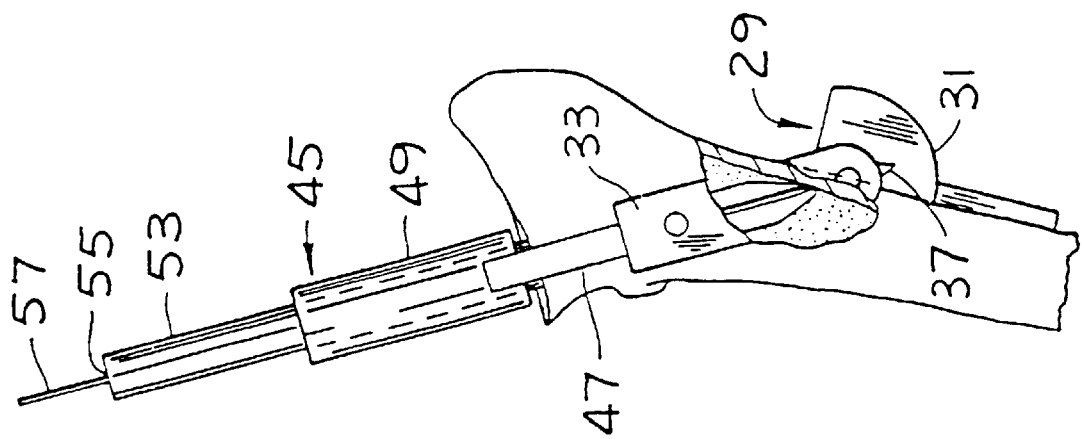
FIG. 4N is a view showing the angle guide, calcar milling guide, cannulated pin guide, trocar point guide pin and drill point guide pin for drilling through the posterolateral femoral cortex.

As shown in FIG. 4N, the cannulated pin guide 53 is received in the calcar miller guide 51 and into the first bore B1 in the medial endosteum. The trocar point guide pin 57 is received in the cannulated pin guide axial passage 55 to make a starter mark on the lateral endosteum. After the starter mark is made, the trocar point guide pin 57 is removed from the passage 55. The drill point guide pin 59 is then received in the cannulated pin guide axial passage 55 and is used to drill through the posterolateral femoral cortex C, forming an oblique hole in the posterolateral femoral cortex. The drill point guide pin 59 is left in place after drilling the oblique hole in the cortex, the cannulated pin guide 53 is removed from the femur F and the calcar miller guide 45 is removed from the guide sleeve 33 of the angle guide 29.

As shown in FIG. 4P, the cannulated cortex drill 61 is received over the drill point guide Dpn 59 to drill through the posterolateral femoral cortex C on the same axis as the first bore B1 milled by the calcar miller 51. Cortex drill 61 drills the oblique hole to a diameter that is smaller than the first bore B1 formed in the femur F. The cannulated cortex drill 61 and the drill point guide pin 59 are then removed from the femur 3.

Figure 4S:
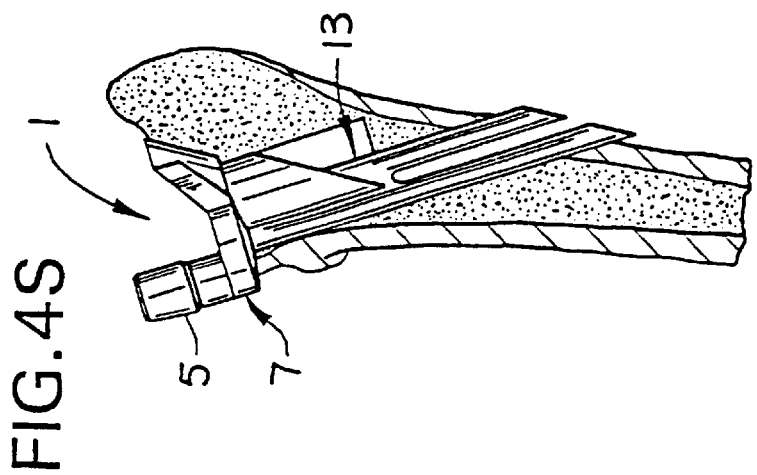
FIG. 4S is a view showing the implanted prosthesis.

The offset reaming guide 63 is then placed into the first bore B1 bullet end first. A first cannulated reamer (not shown) is received on the trunnion 65 to ream the second bore B2 in the femoral neck N which is parallel to the first bore B1. A progression of cannulated reamers (not shown) are used, with each succeeding reamer having a larger diameter. The final cannulated reamer 73 reams the second bore B2 to a diameter which achieves line-to-line contact between the prosthesis 1 and the endosteum (FIG. 4Q). After the second bore B2 is reamed to a depth to accommodate the upper stem portion 15 of the prosthesis 1, the cannulated reamer 73 and the offset reaming guide 63 are removed from the femur F.

Figure 4R:
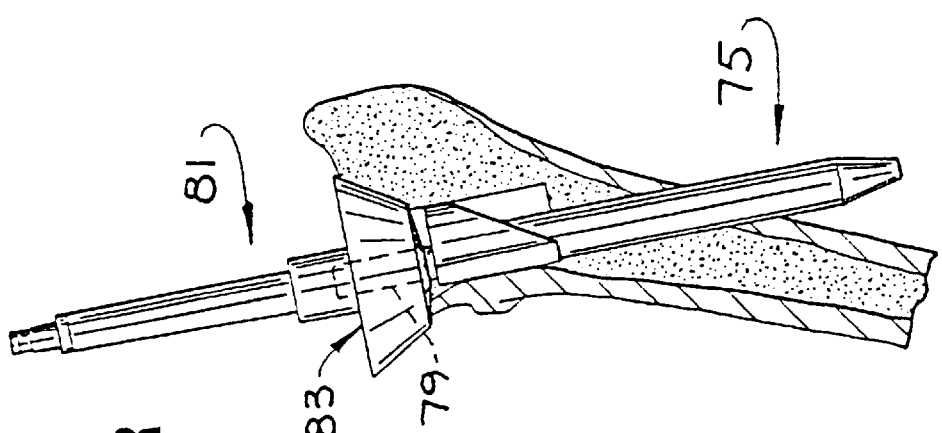
Figure 4Q:
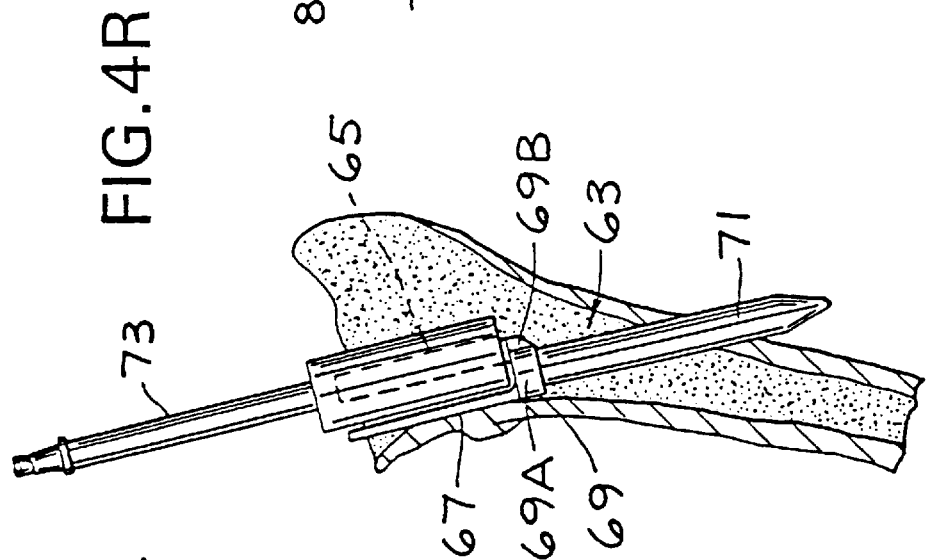
FIG. 4Q is a view showing the offset reaming guide and cannulated reamer for reaming the second bore in the femoral neck.
Figure 5C:
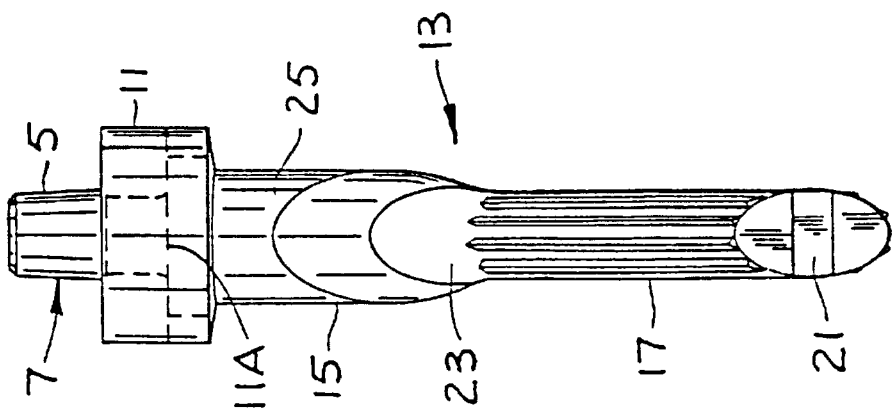
FIG. 5C is a left side elevational view thereof.
Figure 5B:
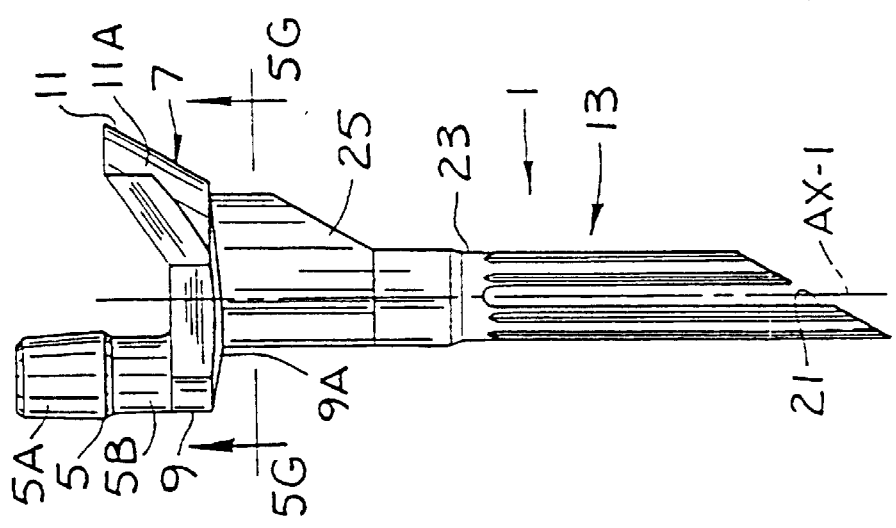
FIG. 5B is a front elevational view thereof.
Figure 5A:
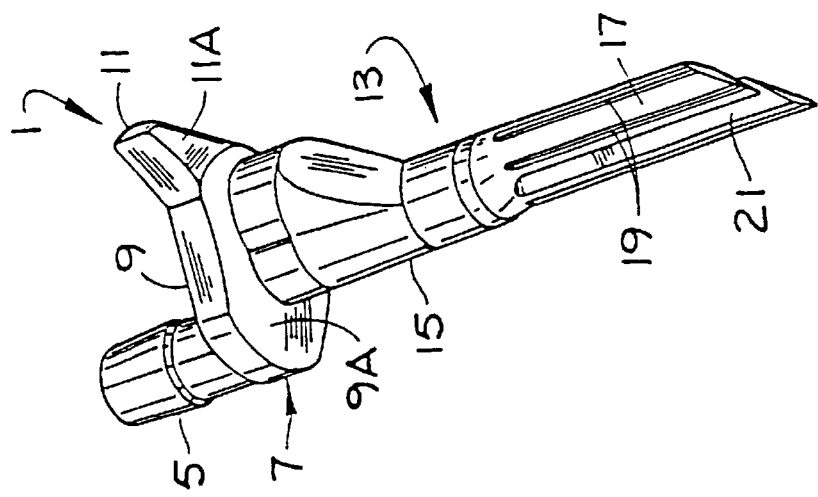
FIG. 5A is a perspective view of the split stem prosthesis of FIG. 1.

Referring to FIG. 4R, the calcar planing guide 75 is inserted into the proximal side of the first bore B1 and through the oblique hole in the posterolateral cortex C. The central longitudinal axis of the trunnion 79 and the stem 77 of the calcar planing guide 75 are collinear with the first bore B1. The calcar planer 81 is then placed on the trunnion 79 and the surface of the femoral neck is planed generally perpendicular to the axis (AX-1) of the first bore S1 while even pressure is applied to the calcar planer to form a seat for the collar 7 of the prosthesis 1. The greater trochanter T is substantially preserved by the calcar planer 81. Only an angled segment of the trochanter T is cut away providing an angled seat for the flange 11 of the collar 7. In this way, a secure engagement of the prosthesis 1 on the cortical bone C of the upper femur is achieved without sacrificing a substantial portion of the trochanter T (FIG. 1).

The bottom 89 of the calcar planer 81 is slightly cupped so that the portion of the seat on the femoral neck N slopes downwardly toward the axis AX-1. The shape of this portion of the seat is complimentary to that of the underside 9A of the prosthesis collar 7. The cup shape of the seat on the femoral neck N helps to locate the prosthesis 1. Moreover, when the underside of the collar 7 and the seat are congruent, the entire area of the seat engages the underside (9A, 11A) of the collar 7 and is subjected to loading by the prosthesis 1. Loading of the bone material of the seat over the entire area of engagement with the collar surface (9A, 11A) prevents resorption (withdrawing) of the bone after the prosthesis 1 is implanted. However, although macroscopic congruence is important, microscopic roughness or porosity of the collar undersurface (9A, 11A) possibly combined with bioactive or chemical coating (e.g., calcium phosphate compound) allows an ingrowth of bone from the seat which facilitates bonding of the collar surface with the seat. Because the collar undersurface (9A, 11A) achieves one hundred percent cortical contact and transmits substantially one hundred percent of the cortical loading, the chemical coating is used only on the underside of the collar 7 and at no locations on the stem 13. After planing, the calcar planer 81 and the calcar planer guide 75 are removed.

The prosthesis 1 (without the ball 3) is then implanted by driving the stem 13 into the first bore B1 as shown in FIG. 4S. The splines 19 of the stem bite into the walls of the first bore B1 and the stem protrudes slightly through the oblique hole so that cortical bone does not later grow over the end of the stem. Growth of bone over the end of the stem 13 would be undesirable since it would impede the ability of the prosthesis 1 to transmit loads from the hip to the upper femur. The upper stem portion 15 fits closely into the first bore B1. The underside 9A of the collar platform 9 is congruent with the portion of the seat which was formed by the bottom 89 of the calcar planer head 83 and the underside 11A of the flange 11 is congruent with the portion of the seat on the trochanter T formed by the side 91 of the calcar planing head.

Once the prosthesis 1 is implanted, an appropriately sized ball 3 is then locked onto the neck.

In a second, lesser preferred embodiment, the procedure is somewhat modified. Referring to FIGS. 4C and 4D, after the femoral neck N is resected, a reamer guide 95 (similar in construction to the calcar miller guide 45) is secured to the guide sleeve 33 of the angle guide 29, which effectively centers the reamer guide over the femoral neck N so that the second bore B2 is formed first. As before, the second bore B2 is formed by a progression of reamers (not shown), with each succeeding reamer having a larger diameter than the preceding reamer. The final reamer 97 has a diameter of 21 mm, so that the femoral neck N is reamed to a diameter of 21 mm. The reamer guide 95 is then removed from the guide sleeve 33, leaving the angle guide 29 attached.

A calcar miller guide 99 having a trunnion 101 is attached to the angle guide 29 and the first bore B1 is formed by milling with a series of calcar millers including final calcar miller 103 (FIGS. 4E and 4F). The angle guide 29 is removed in FIG. 4F to more clearly show the calcar miller guide 99. The calcar miller guide 99 is removed from the angle guide 29 and a drill pin guide 105 is mounted on the angle guide. Referring to FIG. 4G, the upper portion of the drill pin guide 105 has a double cylinder construction similar to the upper portion 15 of the prothesis stem 13 to fit in the first and second bores, 21 and B2. The angle guide 29 is also not shown in FIG. 4G. The same trocar pin 57 and drill pin 59 in the more preferred embodiment are used with the drill pin guide 105 of the lesser preferred embodiment to start the distal hole in the posterolateral cortex of the femur F. The planing step and instrumentation are substantially the same as described for the method of the first more preferred embodiment.

In a third, most preferred embodiment shown in FIGS. 18A–18P, the procedure and some of the tools are modified. The initial step (FIG. 18A) of determining the angle of the medial trabecular stream TS is carried out exactly as described above in reference to FIG. 4A. Once the angle of the medial trabecular stream with respect to the central longitudinal axis AX-3 of the bone is determined, the angle of the guide sleeve 33 of the angle guide 29 is set as described above. In the most preferred embodiment, this angle is checked using a protractor device indicated generally at 101. The protractor device has a stop 103 against which the bracket 31 of the angle guide 29 is placed. A pivotable arm 105 can be moved, by loosening set screw 107, to the angle corresponding to the angle of the medial trabecular stream TS. The arm 105 is fixed by the screw 107 and the guide sleeve 33 should be in face-to-face engagement with the arm. If not, the sleeve guide 33 is turned until it matches the angle of the arm 105 of the protractor device 101. The larger scale of the protractor device 101 permits a more accurate setting of the angle guide 29.

Figure 18D:
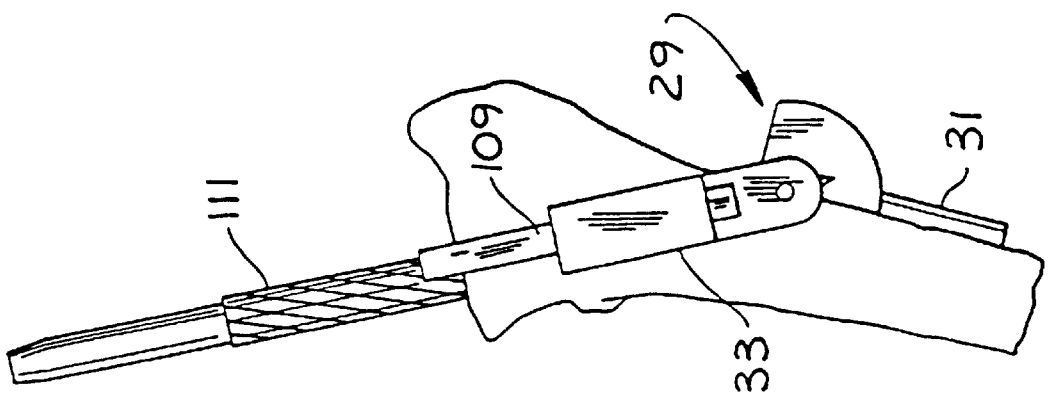
FIG. 18D is a view showing an initial reaming step.
Figure 18C:
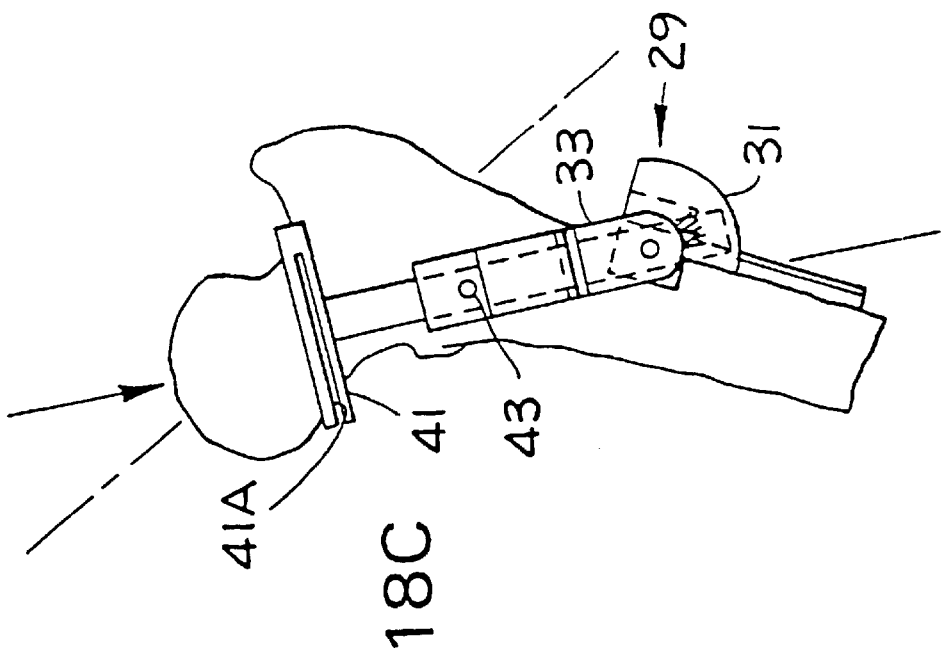
FIG. 18C is a view showing the angle guide and the saw guide around the femur for femoral neck resection.
Figure 18H:
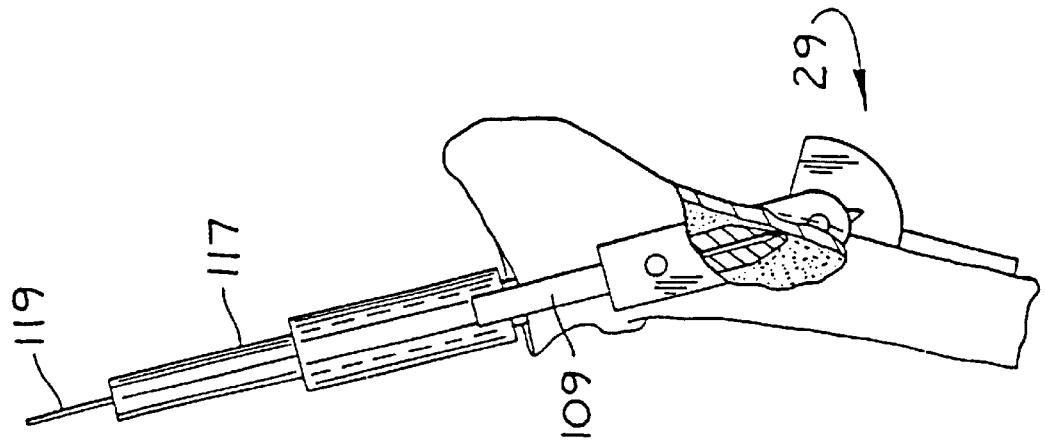
FIG. 18H is a view showing a pin guide and drill point guide pin for use in drilling through the posterolateral femoral cortex.

As illustrated in FIG. 18C, the angle guide 29 is attached to the surgically exposed femur and the saw guide 41 is secured in the angle guide. The procedure for resecting the femoral head is the same as described above in reference to FIG. 4B. The saw guide 41 is removed from the angle bracket and replaced with a visual sighting bar 109 which extends generally upwardly from the guide sleeve 33 and beyond the resected neck N of the femur. As shown in FIGS. 18D and 18E, a reamer 111 is then directed by the surgeon along the angle indicated by the visual sighting bar 109 into the femur to form an initial hole HO in the femur. The hole HO thus formed has a longitudinal axis parallel to the medial trabecular stream TS and with the proper anteversion, both of which are indicated by the bar 109. The reaming may be carried out using a reamer 111 and a number of succeeding reamers of increasingly larger diameter to form the full diameter of the hole. A skilled surgeon can alternatively form the full diameter of the hole HO using only the reamer 111. In that event, the surgeon moves the reamer 11 in progressively larger circles until the full diameter is reached. The final diameter of the hole HO is dictated by the size and shape of the femur of the individual patient.

Sizing of the hole for the best fitting prosthesis is carried out using proximal femoral sizers 113 such as the sizer shown in FIG. 18F. The sizer 113 is substantially identical in shape to the upper portion 15" of the stem 13" of the prosthesis 1" to be implanted. The sizers range in size. For example the larger cylindrical portion 113A of the sizer may range in size from 18 to 26 mm in one millimeter increments. The sizers 113 are inserted into the hole HO parallel to the visual sighting bar 109 (not shown in FIG. 18F). Progressively larger sizers are fitted into the proximal femur to determine the dimensions of the largest prosthesis which will fit in the femur. The surgeon now knows the size of the prosthesis 1" to be implanted and the exact dimension of the bores B1, B2 needed to receive the prosthesis. The prosthesis 1" is selected to be a size larger than the largest sizer 113 which is able to fit in the hole HO. For example, if the largest sizer that would fit had a smaller diameter portion of 14.5 mm a prosthesis having a smaller diameter upper stem portion of 15 mm would be used.

Figure 18G:
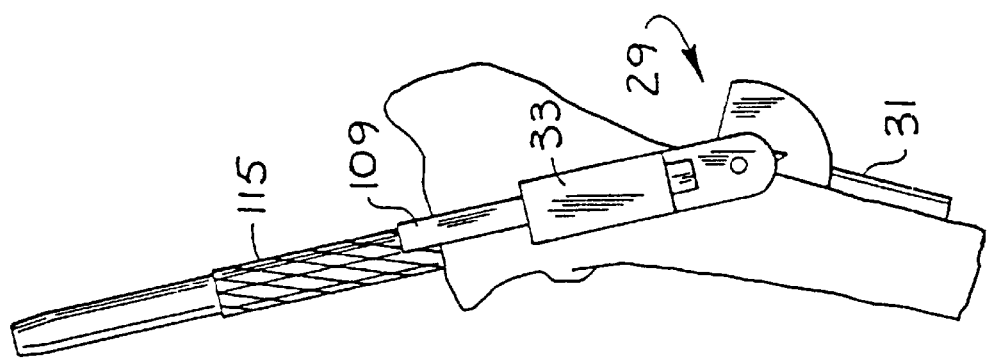
FIG. 18G is a view showing a calcar miller milling the first bore.

A reamer 115 having a diameter corresponding to the final diameter (e.g., 15 mm) of the first bore B1 is selected and used to form the first bore. As shown in FIG. 18G, the reamer is guided freehand using the visual sighting bar 109. The first bore BE is also formed so that at least a portion of the bore is defined by the endosteum of the medial femoral cortex. Thus, the prosthesis 1" when installed will engage the hard cortical bone at this location in the bore B1. In order to drill a hole in the posterolateral femoral cortex which is precisely parallel to the medial trabecular stream TS and with the proper anteversion, a series of one piece, cannulated outrigger pin guides 117 (only one is shown) of different sizes are provided. The pin guide 117 having a diameter corresponding to that of the newly formed bore B1 is selected and inserted into the bore. The outrigger portion of the pin guide 117 is received in the guide sleeve 33 of the angle guide 29 at the same time it is inserted into the bore B1 for the most precise alignment of the pin guide. The tapered tip of the guide is advanced into the first bore B1 until it makes contact with the endosteum of the lateral femoral cortex.

Figure 18J:
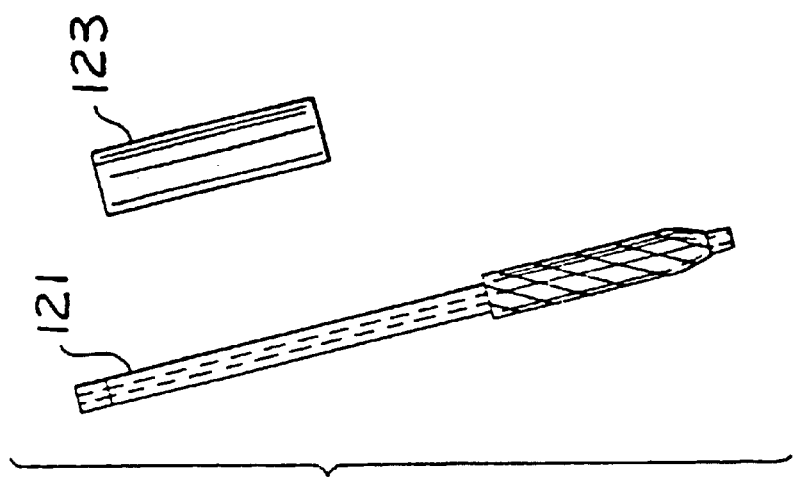
FIG. 18J shows a cortical drill and sleeve used to drill the posterolateral femoral cortex.
Figure 18I:
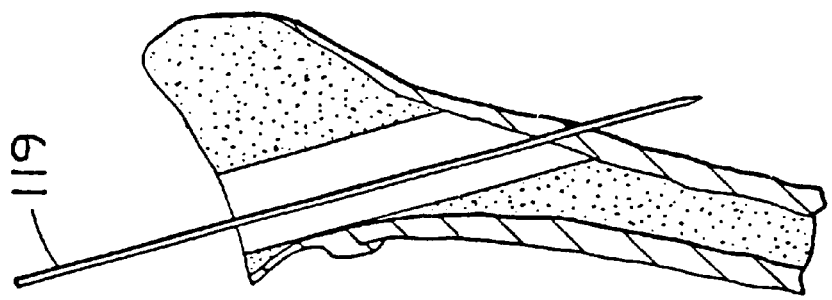
FIG. 18I is a view showing the drill point guide pin after removal of the pin guide.

A drill guide pin 119 is inserted into the pin guide 117. The orientation of the guide pin 119 in the femur is checked by making sure the angle guide 29 is still at the proper angle parallel to the medial trabecular stream TS and with the proper anteversion. Moreover, the pin guide 117 is checked to make sure it is in contact with the endosteal surface of the medial neck cortex. A drill (not shown) is attached to the guide pin 119, and it is drilled through the lateral femoral cortex. As shown in FIG. 18I, the pin guide 117 and the angle bracket 29 are removed from the femur, leaving on the guide pin 119. The next step is to drill the transcortical tunnel through the posterolateral femoral cortex. A cannulated drill 121 is selected which corresponds to the diameter of the lower portion 17" of the prosthesis 1". For example if the diameter of the lower portion 17" is to be 9.5 mm, a 9 mm cannulated drill is selected. As illustrated in FIG. 18J, the cannulated drill 121 comes with a guide ferrule 123 which is sized according to the diameter of the bore B1. Thus as shown in FIG. 18K, the guide ferrule 123 helps (along with the guide pin 119) to align the drill with the longitudinal axis of the bore B1. The cannulated drill 121 slides over the guide pin 119 with the guide ferrule 123 received on the drill and the transcortical tunnel is formed in the posterolateral femoral cortex. Care is taken during drilling to make sure the ferrule 123 remains against the medial endosteal cortex.

Figure 18L:
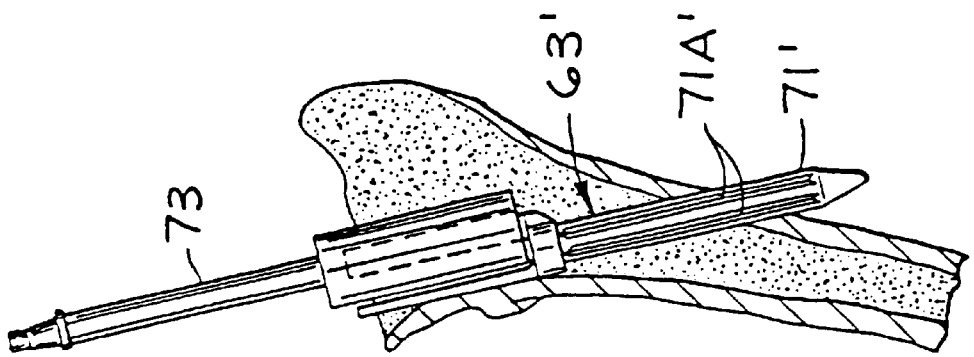
FIG. 18L is a view showing an offset reaming guide and cannulated reamer for reaming the second bore in the femoral neck.
Figure 18K:
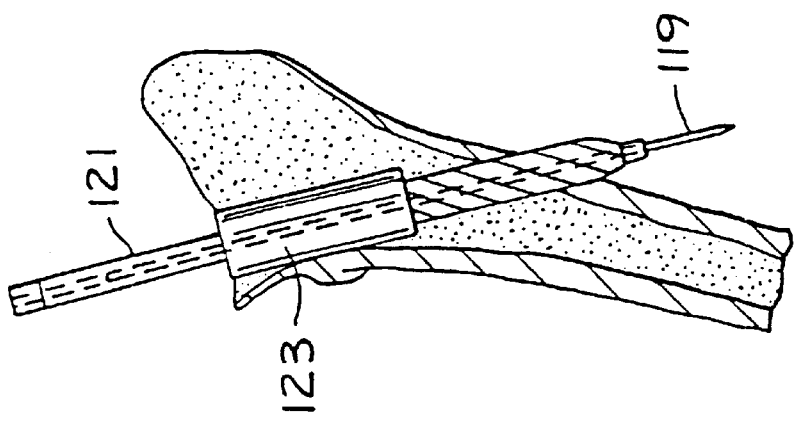
FIG. 18K shows the cortical drill as received on the guide pin after drilling through the posterolateral femoral cortex.

The second bore B2 is formed as shown in FIG. 18L, which is the same procedure as described above in relation to FIG. 4Q. However, an offset reaming guide 63' is shown in FIG. 18L which has splines 71A' for more precise orientation of the reaming guide in the femur.

As shown in FIG. 18M, the calcar planing guide 75' inserted into the bores B1, B2 is virtually identical in shape to the prosthesis 1". The planing guide 75' has splines 77C' on its lower stem portion 77B' like those of the prosthesis. The calcar planer 81' is received on the trunnion 79' of the planing guide 75' and a flat seat is formed on the femoral neck N. There is preferably a very close tolerance between the trunnion 79' and the planer 81' to avoid wobble as the planer is rotated to form the seat.

Referring to FIG. 18N the prosthesis 1" is inserted into the femur using a guide tip 125 which is attached to the end of the prosthesis. More particularly, the guide tip 125 has a stem (not shown) which is received in a hole (not shown) in the distal end of the prosthesis 1". The tip 125 is held by a friction fit in the hole. The bullet nosed shape of the tip 125 helps to keep the prosthesis from hanging up on the bone before it passes through the posterolateral femoral cortex. Once implanted, the tip 125 can be pulled off of the prosthesis 1" as shown in FIG. 18P. The prosthesis 1" is checked to make certain that the collar 7" is fully seated on the seat of the femur neck N, and checked for the appropriate amount of stem protrusion from the femur.

FIGS. 19A–19D illustrate an additional step which may be performed to make absolutely certain that the a collar 7'" of a prosthesis 1'" of still another embodiment has seated fully against the femoral neck N. The prosthesis 1'" differs from the prosthesis 1" only in that the underside 11A'" of its flange 11'" is composed of two intersecting planes. The underside 11A" of the prothesis flange 11" has the shape of a conical section. A saw template, generally indicated at 127, includes a cap 128 capable of fitting on the neck 5'" of the prosthesis 1'". The cap 128 precisely locates slots 29 just under the collar 7'" and to the medial side of the flange 11'".

A saw (e.g., oscillating saw SW) may then be used to cut away additional portions of the femoral neck N under the collar 7'". The saw template 127 guides the saw SW and a reciprocating saw (not shown) for making cuts which are closely congruent with the shape of the underside (9A'", 11A'") of the collar 7'". The planer shape of the underside 11A'" permits linear cuts to be made (e.g., as by the blade B' of the reciprocating saw in FIG. 19D) adjacent to the flange while achieving a high degree of congruency between the cut surface and the flange underside. After removal of these portions, the underside of the collar 7'" is irrigated with remaining debris and the area is checked for completeness of the removal. The prosthesis 1'" is then driven downwardly (e.g., 1 or 2 mm) after the portions are removed for a more congruent seating against the neck N.

Figure 19A:
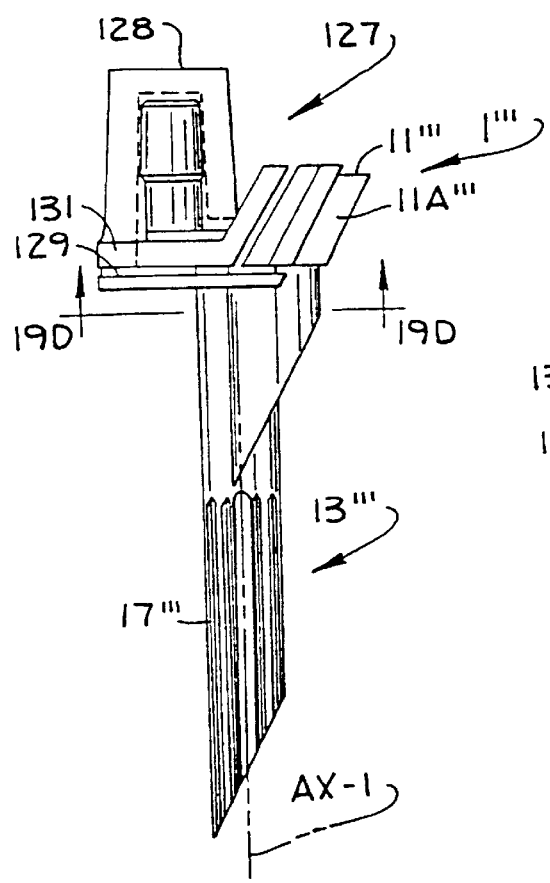
FIG. 19A is a side elevation of a prosthesis having and a saw template mounted on the prosthesis for use in seating the prosthesis.
Figure 19B:
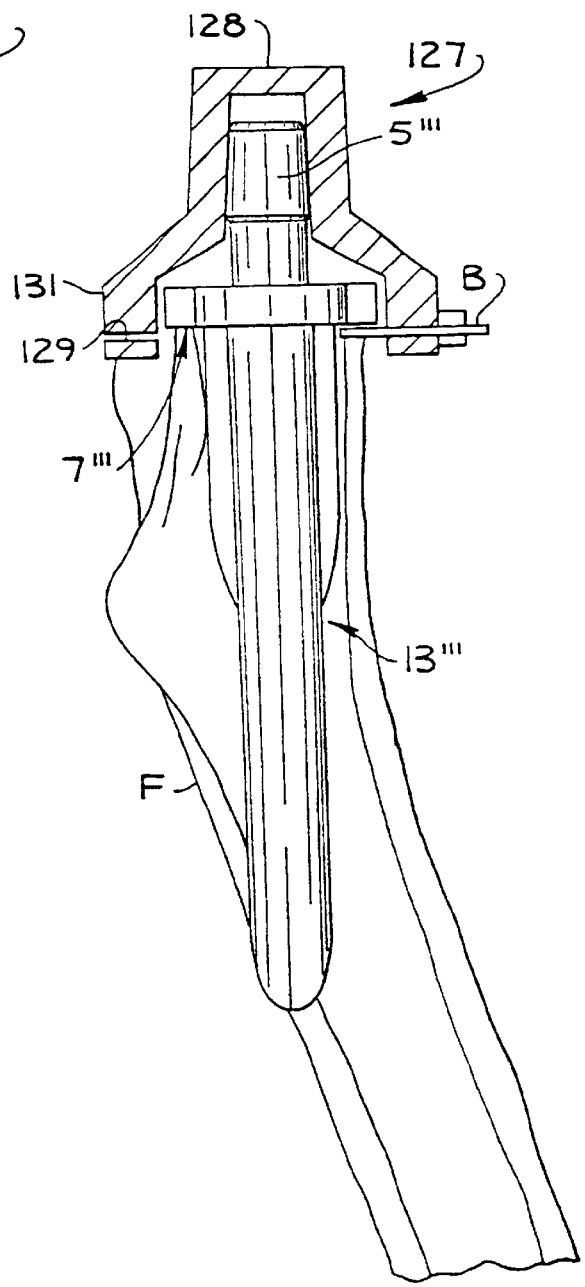
FIG. 19B is a fragmentary cross section of an upper portion of the femur and saw template as shown in FIG. 19A, as seen from a position generally medial of the femur.
Figure 19C:
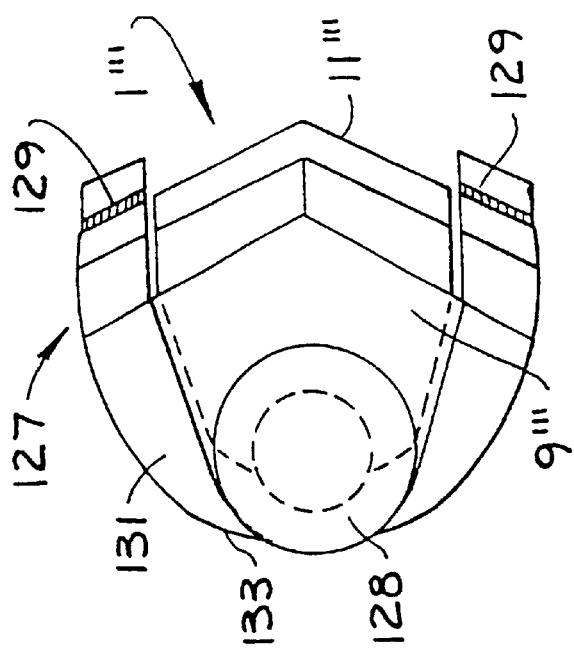
FIG. 19C is a top plan view of the femur and saw template.
Figure 19D:
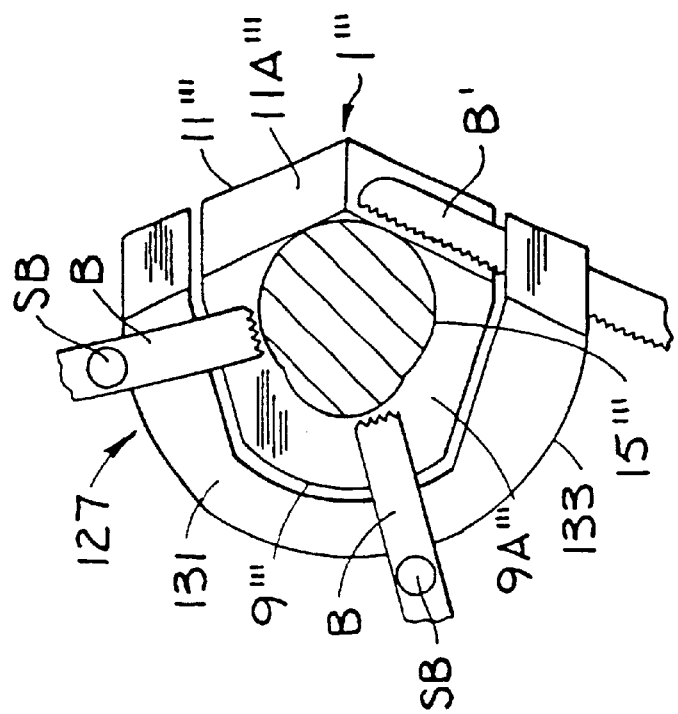
FIG. 19D is a section taken in a plane including line 19D—19D of FIG. 19A.
Figure 20:
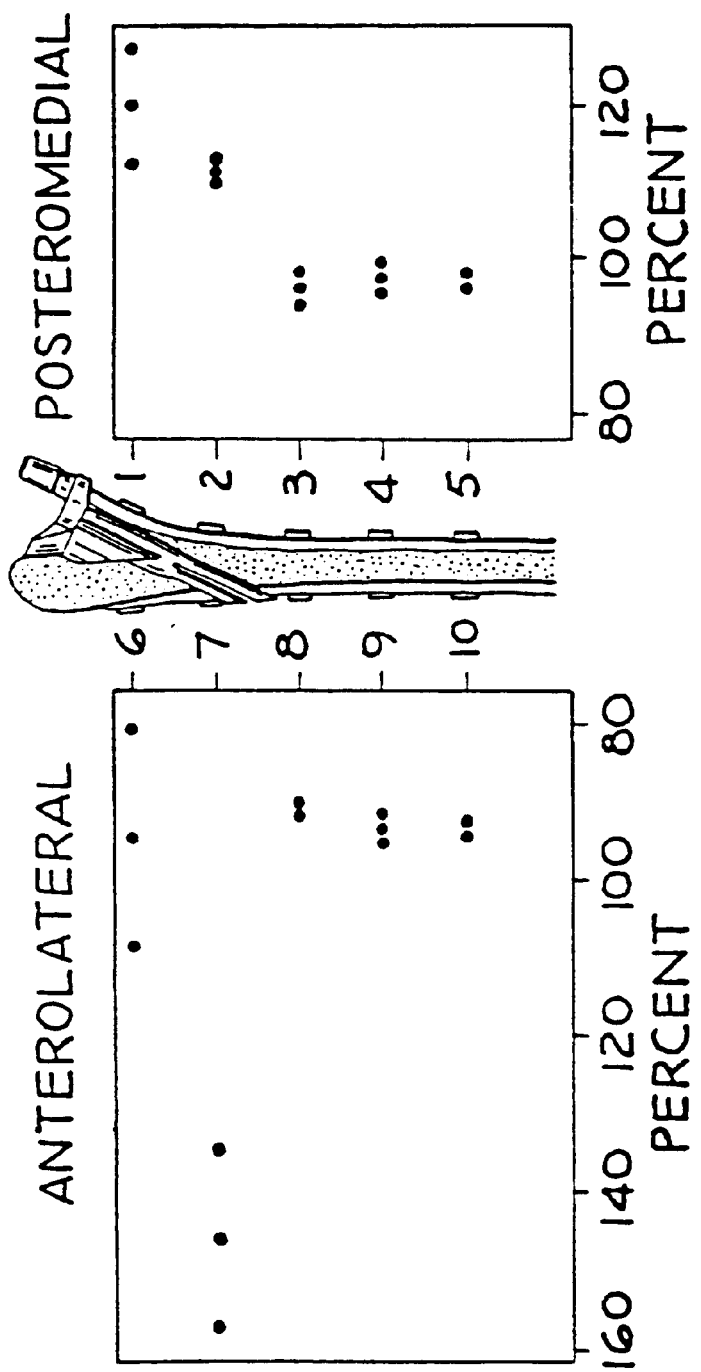
FIG. 20 is a plot of test results on the prosthesis of the present invention.

The slots 129 are disposed in a rim 131 of the saw template 127. Referring to FIG. 19D, the rim 131 has a peripheral edge 133 which is shaped so that the distance of the edge to the upper portion 15'" of the stem 13'" of the prosthesis 1'" is everywhere constant. The peripheral edge 133 is engaged by stop bolts SB on blades B of the saw SW to limit the inward travel of the saw blade. Thus, the shape of the rim 131 assures that the blades B of the saw SW will not contact the upper portion 15'" of the stem 13'".

It is envisioned that the saw template 127 could be used in place of the planing guide (75, 75') and calcar planer (81, 81'). The other steps for implantation of the prosthesis 1'" would be the same as shown in described above for the lesser preferred, more preferred and most preferred methods. However, there is no planing of the neck N after the femoral head H is resected to form a seat for the collar 7'". The prosthesis 1'" is driven into the femur F until the underside (9A'", 11A'") of the collar 7'" engages the neck. The saw template 127 is attached to the prosthesis 1'" and the bone is cut under the collar 7'" to form the seat for the collar. The saw template 127 may also be used beneficially in the removal of a previously implanted prosthesis 1'". Bone ingrowth into the prosthesis 1'" is promoted (as described above) only on the underside (9A'", 11A'") of the collar 7'". Minimal amounts of bone would be removed using the saw template 127 to separate the underside (9A'", 11A'") of the collar 7'" from the femur F.

(d) Study Regarding Present Invention

In total hip arthroplasty (THA), intramedullary stem femoral components decrease strain levels in the proximal femur resulting in periprosthetic bone loss. This study evaluates the strain pattern of the femoral stem design of the present invention in comparison to a normal femur and to conventional femur head-neck prostheses.

Attempts to eliminate strain deprivation bone loss in THA by means of reduced stiffness intramedullary stems have been unsuccessful(1). A human study of an instrumented femoral prosthesis found the load trajectory of the hip to fall within a relatively narrow range of angles(2). An alternative approach to improve proximal femoral loading is to align the femoral stem parallel to the average resultant loading vector of the individual hip. In theory, unimpeded loading of the femoral neck through a stable interface should generate strain levels equivalent to the intact femur. To enable unrestricted collar-neck loading, it is necessary for the implant stem to go through the bone in line with the resultant vector. The purpose of this study was to determine the strain distribution of a transosseous THA prosthesis.

Twelve synthetic femurs were bonded with twelve triaxial rosette strain gages (e.g., strain gages 109 shown in FIG. 1), five each along the posteromedial and anterolateral aspect and one each proximal-anterior and proximal posterior. The femurs were mounted in a single limb stance jig. Spinal loads of 1068 and 2135 Newtons were applied with simulated abductor force of 712 and 1423 Newtons creating a resultant 21° from the femoral shaft axis. Strain data were acquired with a computerized multi-channel system which converted the readings to microstrain.

Prototype cobalt-chrome transosseous femoral stems constructed according to the principles of the present invention were installed and loaded under the same conditions as the intact femurs. The collar was 10° conical and perpendicular to the stem. The proximal stem consisted of two cylindrical elements 23, 25 of 15 and 21 mm diameter, respectively, and achieved tangential contact with the endosteal cortex. The distal stem, which was fluted and 12 mm in diameter, was press-fit through an 11.5 mm hole in the posterolateral cortex. Two distal stem variations were tested in each femur: slotted (n=11) and solid (n=12). Radiographs of each femur were obtained. The angle of implantation varied from 1460 to 1580 in relation to the lateral shaft cortex.

Eight non-cemented and cemented cobalt-chrome intramedullary stems (Replica, 16.5-LG and Response, 13.5, manufactured by DePuy, Inc. of Warsaw, Ind.) were installed and tested.

Analysis of variance was performed on all data.

Comparable strain patterns were noted at each of the two loading conditions. The following results are from the higher load condition. A graphic representation of the results appears as FIG. 18.

The non-cemented and cemented intramedullary stems resulted in proximal posteromedial compression strain levels of 42.7±4.6% (mean±SEM, p=0.0007) and 32.3±2.6% (p=0.0001) compared with the intact condition.

The slotted and solid transosseous stems produced proximal posteromedial compression strain levels of 119.0±7.4% (p=0.36) and 101.1±16.6% (p=0.66). Compression, tension and shear strain levels were generally not significantly different from intact levels. Exceptions included increased tension strain at the most proximal posteromedial gage with the slotted stem, 128.9±2.7% (p=0.029). Significantly increased compression strain was noted at the gage nearest the stem exit site with the slotted and solid stems (146.1±11.2%, p=0.0096 and 188.6±11.9%, p=0.0006). A trend was noted of higher proximal strain levels with a more horizontal angle of implantation, however this was not significant on linear regression analysis.

The diminished strain levels noted with the intramedullary stem femoral components were consistent with those previously reported(3). Although significant effort has been expended attempting to resolve the "modulus mismatch" of intramedullary stems, the results of this study suggest that a trajectory mismatch may be a more significant factor in strain reduction. The compression trabeculae of the hip were found to be 10 to 40° more horizontal than the axis of the femoral shaft(4). The consequent bending moment on intramedullary stem components impedes proximal interface loading. The loading trajectory of the hip is more horizontal than intramedullary stem insertion trajectory (femoral shaft axis) which creates a bending moment.

A trajectory matched femoral component (stem aligned with loading vector) incurs a smaller bending moment and receives a more axial load transmission. The cylindrical machining and corresponding stem of this transosseous design seeks to resist rotation and toggle with proximal and distal cortical contact/macrointerlock, but accommodates collar-neck interface compression. Although proximal femoral strain levels were restored with this prototype, high strain levels near the distal stem would raise concern for potential thigh pain.

Within a synthetic femur strain model, transosseous THA femoral components demonstrated higher proximal femoral strain levels than intramedullary stems.

REFERENCES (1) Bobyn, J. D. et al.: CORR 261:196, 1990
(2) Davy, D. T. et al.: JBJS 70A:45, 1988
(3) Oh, I. and Harris, W. H.: JBJS 60A:75, 1978
(4) Clark, J. M. et al.: J Arthr 2:99, 1987

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A femoral prosthesis for implantation in a femur, the prosthesis comprising a neck adapted to receive a ball thereon, a collar on which the neck is mounted and a stem extending from the collar on the opposite side of the collar from the neck, the prosthesis having a longitudinal axis corresponding to the longitudinal axis of the stem and being configured for transosseous implantation in which the stem enters the bone generally at one side thereof, crosses a medullary canal and enters cortical bone on an opposite side of the bone, the stem being constructed and arranged to fix the prosthesis from movement about its longitudinal axis and about axes perpendicular to the longitudinal axis and to inhibit axial fixation of the stem upon implantation in the femur, thereby to achieve substantially natural loading of the upper femur.

2. A femoral prosthesis as set forth in claim 1 wherein the stem comprises outwardly facing fixation surfaces for fixing the prosthesis to the femur, the fixation surfaces being generally parallel to the longitudinal axis of the prosthesis.

3. A femoral prosthesis as set forth in claim 2 wherein an upper stem portion has the shape of two parallel, partially radially overlapping cylinders.

4. A femoral prosthesis as set forth in claim 2 wherein the stem has axially extending splines formed thereon for fixing the prosthesis from movement about its longitudinal axis and about axes perpendicular to the longitudinal axis and to inhibit axial fixation of the stem upon implantation in a femur.

5. A femoral prosthesis as set forth in claim 2 wherein the stem includes an upper portion, fixation surfaces of the upper portion being substantially smooth to inhibit bone ingrowth into the fixation surfaces of the upper portion.

6. A femoral prosthesis as set forth in claim 5 wherein the stem has axially extending splines formed thereon for fixing the prosthesis from movement about its longitudinal axis and about axes perpendicular to the longitudinal axis and formed to inhibit axial fixation of the prosthesis upon implantation in a femur.

7. A femoral prosthesis as set forth in claim 1 wherein the collar has an underside constructed and arranged for engaging the upper femur for transmitting loads to the upper femur, the collar comprising a first portion and a second portion, an underside of the second portion engageable with the femur being oriented at an angle to an underside of the first portion.

8. A femoral prosthesis as set forth in claim 7 wherein the first portion of the collar comprises a neck platform on which the neck is mounted, and the second portion of the collar comprises a flange disposed for engaging the greater trochanter of the femur.

9. A femoral prosthesis as set forth in claim 7 wherein the undersides of the first and second portions of the collar are of a porous construction to encourage bone ingrowth into the collar, the remainder of the prosthesis being free of porous construction.

10. A femoral prosthesis as set forth in claim 1 wherein the collar is sized and shaped to cap the medullary canal of the femur exposed after resection of the femoral head thereby to prevent migration of debris into the medullary canal.

11. A femoral prosthesis as set forth in claim 1 wherein the neck has a longitudinal axis parallel to the longitudinal axis of the stem.

12. A femoral prosthesis as set forth in claim 1 in combination with the ball.

13. A femoral prosthesis as set forth in claim 1 in combination with a calcar planing guide adapted for use in planing a surface of the femur to form a seat, the planing guide including a stem sized and shaped substantially identically to the stem of the prosthesis stem thereby to facilitate precise planing of the femur surface to form the seat, an upper portion of the planing guide stem having the shape of two parallel, partially radially overlapping cylinders.

14. A femoral prosthesis as set forth in claim 1 in combination with a saw template constructed for mounting on the neck of the prosthesis, the saw template having a saw guide slot positioned when mounted on the neck for precise sawing of the femur under the prosthesis collar to remove bone and facilitate a congruent fitting of the collar on the femur.

15. A femoral prosthesis as set forth in claim 1 wherein the stem has axially extending splines formed thereon for engaging the femoral bone and fixing the prosthesis from movement about its longitudinal axis and about axes perpendicular to the longitudinal axis and to inhibit axial fixation of the stem upon implantation in a femur.

16. A femoral prosthesis as set forth in claim 1 wherein the neck, collar and stem are integrally made of one piece of material.

17. A femoral prosthesis for implantation in a femur, the prosthesis comprising a neck adapted to receive a ball thereon, a collar on which the neck is mounted and a stem extending from the collar on the opposite side of the collar from the neck, the prosthesis having a longitudinal axis corresponding to the longitudinal axis of the stem, the neck having a longitudinal axis parallel to the longitudinal axis of the stem, the collar being continuous about the circumference of the prosthesis, extending outwardly laterally, anteriorly, medially and posteriorly and sized and shaped to cap the medullary canal of the femur exposed after resection of the femur thereby to prevent migration of joint wear debris into the medullary canal.

18. A femoral prosthesis as set forth in claim 17 wherein the collar has an underside constructed and arranged for engaging the upper femur for transmitting loads to the upper femur, the collar comprising a first portion and a second portion, an underside of the second portion engageable with the femur being oriented at an angle to an underside of the first portion.

19. A femoral prosthesis as set forth in claim 18 wherein the first portion of the collar comprises a neck platform on which the neck is mounted, and the second portion of the collar comprises a flange disposed for engaging the trochanter of the femur.

20. A femoral prosthesis as set forth in claim 18 wherein the undersides of the first and second portions of the collar are of a porous construction to encourage bone ingrowth into the collar, the remainder of the prosthesis being free of porous construction.

21. A method for implanting a non-cemented femoral head-neck prosthesis in a femur, the femur having a shaft and a neck at the upper end of the shaft at the medial side of the femur, the method comprising the steps of:
   determining the axis of the medial trabecular stream of the femur;
   cutting the neck of the femur to form a seat on the femur neck;
   drilling a first bore along a line through the shaft of the femur to extend from the neck of the femur down toward the lateral side of the femur along a line substantially parallel to the axis of the medial trabecular stream;
   drilling a second bore through the shaft of the femur to extend from the neck of the femur down toward the lateral side of the femur along a line substantially parallel to the axis of the medial trabecular stream but spaced from the line of the first bore;
   inserting a stem of the prosthesis in one of the first and second bores extending through the shaft to the lateral side of the femur, a portion of the stem being received in the other of the first and second bores.

22. A method as set forth in claim 21 further comprising the steps of providing a prosthesis having a neck with a longitudinal axis parallel to a longitudinal axis of the stem of the prosthesis, and installing the prosthesis in the first and second bores so that the longitudinal axes of the stem and neck are parallel to the medial trabecular stream.

23. A method as set forth in claim 21 wherein the step of inserting the stem comprises driving the stem through said one bore until a distal end of the stem protrudes from the lateral side of the femur.

24. A method as set forth in claim 21 wherein the first and second bores have generally cylindrical walls and together have a shape in cross section of partially radially overlapping cylinders, the portions of the stem contacting the bore walls being generally cylindrically shaped.

25. A method as set forth in claim 21 further comprising the step, following the step of cutting the neck, of milling the neck to shape the seat, the milling cutting a trochanter of the femur at an angle to provide a seat for the prosthesis while preserving most of the trochanter.

26. A method as set forth in claim 21 further comprising the steps of:
   mounting a saw template on the prosthesis as inserted into the femur;
   cutting the femur neck under a collar of the prosthesis using the saw template to form surfaces on the neck corresponding in shape to the underside of the collar;
   driving the prosthesis down onto the surfaces formed.

27. A bone prosthesis for implanting in a bone at a joint, the prosthesis comprising a neck adapted to receive a ball, a collar on which the neck is mounted and a stem extending from the collar on the opposite side of the collar from the neck, the prosthesis having a longitudinal axis corresponding to the longitudinal axis of the stem and being configured for transosseous implantation in which the stem enters the bone generally at one side thereof, crosses a medullary canal and enters cortical bone on an opposite side of the bone, the stem being constructed and arranged to fix the prosthesis from movement relative to the bone about its longitudinal axis and about axes perpendicular to the longitudinal axis and to inhibit axial fixation of the stem upon implantation in the bone.

28. A femoral prosthesis for implantation in a femur, the prosthesis comprising a neck adapted to receive a ball thereon, a collar on which the neck is mounted and a stem extending from the collar on the opposite side of the collar from the neck, the prosthesis having a longitudinal axis corresponding to the longitudinal axis of the stem, the neck having a longitudinal axis parallel to the longitudinal axis of the stem thereby to achieve substantially natural loading of the upper femur.

29. A femoral prosthesis for implantation in a femur, the prosthesis comprising a neck adapted to receive a ball thereon, a collar on which the neck is mounted and a stem extending from the collar on the opposite side of the collar from the neck, an upper portion of the stem having the shape of two parallel, partially radially overlapping elements.

* * * * *

UNITED STATES PATENT AND TRADEMARK OFFICE
CERTIFICATE OF CORRECTION

PATENT NO. : 6,273,915 B1
DATED : August 14, 2001
INVENTOR(S) : James B. Grimes

It is certified that error appears in the above-identified patent and that said Letters Patent is hereby corrected as shown below:

Column 1,
Line 53, "enerally" should read -- generally --.

Column 4,
Line 1, "he" should read -- the --.
Line 67, "Fig. 5E" should read -- Fig. 5B --.

Column 7,
Line 17, "SB" should read -- 5B --.

Column 9,
Line 8, "3B, B2" should read -- B1, B2 --.

Column 10,
Line 31, "21" should read -- B1 --

Column 11,
Line 56, "100" should read -- 10° --.

Column 13,
Line 63, "Dpn 59" should read -- pin 59 --.

Column 14,
Line 23, "S1" should read -- B1 --.

Column 15,
Line 29, "21" should read -- B1 --.

Column 16,
Line 35, "BE" should read -- B1 --.

UNITED STATES PATENT AND TRADEMARK OFFICE
CERTIFICATE OF CORRECTION

PATENT NO. : 6,273,915 B1
DATED : August 14, 2001
INVENTOR(S) : James B. Grimes

It is certified that error appears in the above-identified patent and that said Letters Patent is hereby corrected as shown below:

Column 17,
Line 47, "29" should read -- 129 --.

Column 18,
Lines 66-67, "1460 to 1580" should read -- 146° to 158° --.

Signed and Sealed this

Eighteenth Day of June, 2002

*Attest:*

*Attesting Officer*

JAMES E. ROGAN
*Director of the United States Patent and Trademark Office*